(12) United States Patent
Mochizuki et al.

(10) Patent No.: US 10,155,867 B2
(45) Date of Patent: Dec. 18, 2018

(54) METHOD FOR PRODUCING HALOGENATED ORGANIC PIGMENT, HALOGENATED ORGANIC PIGMENT OBTAINED BY THE PRODUCTION METHOD, AND COLORED COMPOSITION COMPRISING THE SAME

(71) Applicants: TOYO INK SC HOLDINGS CO., LTD., Chuo-ku (JP); TOYOCOLOR CO., LTD., Chuo-ku (JP)

(72) Inventors: Akimitsu Mochizuki, Tokyo (JP); Noriyoshi Takahata, Tokyo (JP); Naoki Hamada, Tokyo (JP); Takashi Kasuya, Tokyo (JP)

(73) Assignees: TOYO INK SC HOLDINGS CO., LTD., Chuo-ku (JP); TOYOCOLOR CO., LTD., Chuo-ku (JP)

( * ) Notice: Subject to any disclaimer, the term of this patent is extended or adjusted under 35 U.S.C. 154(b) by 108 days.

(21) Appl. No.: 14/910,579

(22) PCT Filed: Mar. 25, 2014

(86) PCT No.: PCT/JP2014/058343
§ 371 (c)(1),
(2) Date: Feb. 5, 2016

(87) PCT Pub. No.: WO2015/019659
PCT Pub. Date: Feb. 12, 2015

(65) Prior Publication Data
US 2016/0177100 A1 Jun. 23, 2016

(30) Foreign Application Priority Data

Aug. 5, 2013 (JP) ................................ 2013-162396
Mar. 24, 2014 (JP) ................................ 2014-060231

(51) Int. Cl.
| | |
|---|---|
| *C07D 209/50* | (2006.01) |
| *C07D 401/14* | (2006.01) |
| *C07D 471/04* | (2006.01) |
| *C07D 498/22* | (2006.01) |
| *C07F 1/08* | (2006.01) |
| *C09B 1/00* | (2006.01) |
| *C09B 5/48* | (2006.01) |

(Continued)

(52) U.S. Cl.
CPC ............ *C09B 68/44* (2013.01); *C07D 209/50* (2013.01); *C07D 401/14* (2013.01); *C07D 471/04* (2013.01); *C07D 498/22* (2013.01); *C07F 1/08* (2013.01); *C09B 1/00* (2013.01); *C09B 5/48* (2013.01); *C09B 5/62* (2013.01); *C09B 19/02* (2013.01); *C09B 25/00* (2013.01); *C09B 47/061* (2013.01); *C09B 47/0671* (2013.01); *C09B 47/10* (2013.01); *C09B 47/14* (2013.01); *C09B 48/00* (2013.01); *C09B 57/04* (2013.01); *C09D 11/106* (2013.01); *C09D 11/322* (2013.01); *G02B 1/04* (2013.01); *G03F 7/0007* (2013.01); *G03F 7/105* (2013.01); *G03G 9/092* (2013.01); *G03G 9/0906* (2013.01); *G03G 9/0918* (2013.01); *G03G 9/0922* (2013.01); *G03G 9/0926* (2013.01); *G02B 5/201* (2013.01); *G02B 5/223* (2013.01); *G03F 7/027* (2013.01)

(58) Field of Classification Search
CPC .......... C09B 68/44; C09B 48/00; C09B 5/48; C09B 5/62; C09B 19/02; C09B 25/00; C09B 47/061; C09B 47/10; C09B 47/14; C09B 57/04; C09B 1/00; C09D 11/106; C09D 11/322; C07D 209/50; C07D 401/14; C07D 471/04; C07D 498/22; C07F 1/08; G02B 1/04; G02B 5/201; G02B 5/223; G03G 9/0926; G03G 9/0906; G03G 9/0918; G03G 9/092; G03G 9/0922; G03F 7/0007; G03F 7/105; G03F 7/027
See application file for complete search history.

(56) References Cited

U.S. PATENT DOCUMENTS

| | | | |
|---|---|---|---|
| 4,256,507 A | 3/1981 | Kranz et al. | |
| 4,310,359 A | 1/1982 | Ehashi et al. | |

(Continued)

FOREIGN PATENT DOCUMENTS

| | | |
|---|---|---|
| CN | 1360617 A | 7/2002 |
| CN | 1823141 A | 8/2006 |

(Continued)

OTHER PUBLICATIONS

Machine English translation of JP 2000-186225, Akumatsu et al., Jul. 2000.*

(Continued)

*Primary Examiner* — Patrick D Niland
(74) *Attorney, Agent, or Firm* — Oblon, McClelland, Maier & Neustadt, L.L.P.

(57) ABSTRACT

A method for producing a halogenated organic pigment comprising a halogenation step of halogenating an organic pigment with a halogenating agent, wherein the halogenating agent comprises one or more N-haloimide compounds selected from the group consisting of trichloroisocyanuric acid, a metal salt of dichloroisocyanuric acid, tribromoisocyanuric acid, and a metal salt of dibromoisocyanuric acid. According to the present invention, a method for producing a halogenated organic pigment which does not use high toxic raw materials, does not generate a large amount of unfavorable by-products such as hydrogen halide gas and succinimide, and is excellent in terms of safety and productivity can be provided.

6 Claims, No Drawings

(51) Int. Cl.
*C09B 5/62* (2006.01)
*C09B 19/02* (2006.01)
*C09B 25/00* (2006.01)
*C09B 47/06* (2006.01)
*C09B 47/067* (2006.01)
*C09B 47/10* (2006.01)
*C09B 47/14* (2006.01)
*C09B 48/00* (2006.01)
*C09B 57/04* (2006.01)
*C09B 67/00* (2006.01)
*C09D 11/106* (2014.01)
*C09D 11/322* (2014.01)
*G02B 1/04* (2006.01)
*G02B 5/20* (2006.01)
*G02B 5/22* (2006.01)
*G03F 7/00* (2006.01)
*G03F 7/027* (2006.01)
*G03F 7/105* (2006.01)
*G03G 9/09* (2006.01)

(56) References Cited

U.S. PATENT DOCUMENTS

| | | | |
|---|---|---|---|
| 6,911,074 B2 | 6/2005 | Grandidier et al. | |
| 7,166,158 B2 * | 1/2007 | Mitina | C09B 48/00 |
| | | | 106/31.77 |
| 2002/0117080 A1 | 8/2002 | Okutsu et al. | |
| 2005/0011403 A1 | 1/2005 | Mitina et al. | |
| 2005/0039274 A1 | 2/2005 | Yang et al. | |
| 2006/0281924 A1 | 12/2006 | Yang et al. | |
| 2007/0055071 A1 | 3/2007 | Kimura et al. | |
| 2008/0145772 A1 | 6/2008 | Lee et al. | |
| 2008/0173847 A1 | 7/2008 | Yang et al. | |
| 2009/0135350 A1 | 5/2009 | Shibatani et al. | |
| 2011/0178199 A1 * | 7/2011 | Enomura | B01F 3/0807 |
| | | | 522/3 |

FOREIGN PATENT DOCUMENTS

| | | |
|---|---|---|
| CN | 101206398 A | 6/2008 |
| CN | 100467543 C | 3/2009 |
| CN | 101493538 A | 7/2009 |
| JP | 50-004019 B | 2/1975 |
| JP | 55-105466 | 8/1980 |
| JP | 55-108466 A | 8/1980 |
| JP | 56-118462 A | 9/1981 |
| JP | 64-002063 A | 1/1989 |
| JP | 07-292271 A | 11/1995 |
| JP | 2000-186225 A | 7/2000 |
| JP | 2002-250812 A | 9/2002 |
| JP | 2005-206630 A | 8/2005 |
| JP | 2006-265154 A | 10/2006 |
| JP | 2006-290982 A | 10/2006 |
| JP | 2007-500254 A | 1/2007 |
| JP | 2007-70476 | 3/2007 |
| JP | 2007-533773 A | 11/2007 |
| JP | 2008-38061 A | 2/2008 |
| JP | 2009-137890 | 6/2009 |
| JP | 2013-47336 A | 3/2013 |
| WO | 2005/017046 A2 | 2/2005 |
| WO | 2012/095790 A1 | 7/2012 |

OTHER PUBLICATIONS

Office Action dated Sep. 21, 2017 in the counterpart Chinese application No. 201480043915.9.
Wang Jingbo, "Recent Productino Technology for Phthslocyanine Pigment", pp. 57-62, Dye and Dyeing No. 4, Partial Translation.
Shen Yongjia et at, "Isoindolinone and Isoindolinone Organic Pigment", pp. 7-11, Chemical Technology Market No. 9, Partial Translation.
Extended European Search Report dated Mar. 3, 2017 in Application No. 14835310.5.
Combined Chinese Office Action and Search Report dated Mar. 13, 2017 in Application No. 2014800439159 (with English language translation).
Combined Chinese Office Action and Search Report dated Jul. 6, 2016 in Patent Application No. 201480043915.9 (with English language translation).
International Search Report dated Jun. 24, 2014 for PCT/JP2014/058343 filed on Mar. 25, 2014.
Japanese Office Action dated Jul. 4, 2017 in Japanese Patent Application No. 2014-060231 (with unedited computer generated English translation).
International Preliminary Report on Patentability and Written Opinion dated Feb. 18, 2016 in PCT/JP2014/058343 (English translation only, references previously filed).
Office Action dated Sep. 3, 2013 in Japanese Patent Application No. 2013-162396 (with English translation).
Office Action dated Jun. 12, 2018 in European Patent Application No. 14 835 310.5.
Official Action dated Jul. 24, 2018, in the counterpart Indian Patent Application No. 201617006130.

* cited by examiner

METHOD FOR PRODUCING HALOGENATED ORGANIC PIGMENT, HALOGENATED ORGANIC PIGMENT OBTAINED BY THE PRODUCTION METHOD, AND COLORED COMPOSITION COMPRISING THE SAME

CROSS-REFERENCE TO RELATED APPLICATIONS

This application is a National Stage of PCT/JP2014/058343, which was filed on Mar. 25, 2014 This application is based upon and claims the benefit of priority to Japanese Application No. 2014-060231, which was filed on Mar. 24, 2014, and to Japanese Application No. 2013-162396, which was filed on Aug. 5, 2013.

TECHNICAL FIELD

The present invention relates to a method for producing a halogenated organic pigment. More specifically, the present invention relates to a method for producing a halogenated organic pigment, which is excellent in terms of safety and productivity, wherein the method comprises halogenation of an organic pigment with a specific N-haloimide compound. In addition, the present invention also relates to a halogenated organic pigment obtained by the aforementioned production method, a colored composition comprising the same, and the like.

BACKGROUND ART

Because of the usefulness as a coloring material, organic pigments have been used as a colored composition for an extremely wide range of applications such as offset ink, gravure ink, flexographic ink, plastic colorant, coating material, color toner, color filter resist ink for color filters, and inkjet ink. Depending on the intended application, these organic pigments are required to have coloring properties such as coloring strength, brightness and hue, durabilities such as lightfastness, heat resistance, acid resistance, alkali resistance, solvent resistance and migration resistance, and properties such as dispersibility and fluidity.

For these reasons, in order to adjust hue and to improve durability such as weather resistance, lightfastness, heat resistance and drug resistance, a halogenated organic pigment comprising halogen in the structure thereof has been frequently used. Examples of a representative halogenated organic pigment include a halogenated quinacridone pigment, C. I. Pigment Blue 15:1, C. I. Pigment Blue 15:2, C. I. Pigment Green 7, C. I. Pigment Green 36, C. I. Pigment Violet 23, C. I. Pigment Red 254, C. I. Pigment Yellow 138, C. I. Pigment Yellow 109, and C. I. Pigment Yellow 110 (Non Patent Literature 1).

The "halogenated quinacridone pigment" is a generic name for compounds, each of which has quino[2,3-b]acridine-7,14 (5H,12H)-dione as a basic structure, and some of hydrogen atoms of which are substituted with halogen atoms. As described in Non Patent Literature 1, as examples of such a halogenated quinacridone pigment, 2,9-dichloroquinacridone and 3,10-dichloroquinacridone are registered as C. I. Pigment Red 202 and C. I. Pigment Red 209, respectively, in the database of Color Index International. In addition, a solid solution of unsubstituted quinacridone and 4,11-dichloroquinacridone is registered and disclosed as C. I. Pigment Red 207.

Moreover, as halogenated quinacridones other than the above-mentioned halogenated quinacridone pigments, 3,10-dichloroquinacridone sodium sulfonate and phthalimidomethylated 3,10-dichloroquinacridone are disclosed in Patent Literature 1, and this publication describes that these halogenated quinacridone pigments are used as pigment dispersion aid in inks for ink jetting.

As quinacridone compounds other than these halogenated quinacridones, an unsubstituted quinacridone that is quino [2,3-b]acridine-7,14 (5H,12H)-dione itself, and 2,9-dimethylquinacridone in which two methyl groups are substituted are known as C. I. Pigment Violet 19 and C. I. Pigment Red 122, respectively. Moreover, Patent Literature 2 discloses a quinacridone in which a phthalimidomethyl group is substituted; Patent Literature 3 discloses a quinacridone in which a sulfonic acid group is substituted; and Patent Literature 4 discloses a quinacridone in which a $-SO_2NH-(CH_2)_3-N(C_2H_5)_2$ group is substituted.

The basic structure of quino[2,3-b]acridine-7,14 (5H, 12H)-dione possessed by the quinacridone compound is a comparatively simple chemical structure. Thus, for using such a quinacridone compound as a pigment, there have been essential problems in that the adjustable range of color tone is narrow, and in that it is difficult to prepare fine particles because of its good crystallinity. However, as the aforementioned C. I. Pigment Red 207, many types of solid solution pigments have been found in which two or more types of quinacridones, which comprise dichloroquinacridone as a main body, are homogeneously mixed with one another. As a result, the range of color tone has been widened, and at the same time, it has become easier to prepare fine pigment particles because crystallinity has been reduced due to being a mixture, and it has started to be used for applications requiring extremely fine particles such as color toner, inkjet ink, and color filter resist ink. Furthermore, in regards to quinacridones used as pigment dispersion aid, many types of halogenated quinacridones that are prepared by introducing a phthalimidomethyl group or a sulfonic acid group into a dichloroquinacridone have also been found as described above.

As mentioned above, a halogenated quinacridone, into which one or more halogen atoms are introduced, has become more and more of an industrially important compound. Under such circumstances, problems regarding their production have drawn attention. For example, a chloroaniline used as a starting raw material for production of a chlorinated quinacridone has been problematic regarding safety because it is suspected to be carcinogenic. This chlorinated quinacridone is comparatively expensive as an industrial chemical, and is scarcely available. Moreover, when a chlorinated quinacridone is produced using such a chloroaniline as a starting raw material, there is a problem with productivity in that a total yield becomes low in comparison to the case of producing an unsubstituted quinacridone using aniline as a starting raw material.

Furthermore, chlorinated quinacridones that are industrially produced are substantially only a dichloroquinacridone and a solid solution thereof. When they are used in a colored composition for an ink, a coating material, a plastic material, color toner, inkjet ink, or color filter resist ink, etc., there are problems in that the adjustable range of color tone is still narrow, and it is difficult to prepare into fine particles.

The above-described halogenated organic pigment comprising a halogenated quinacridone can be produced by various methods. Those methods can be broadly categorized into production methods in which an organic pigment serving as a mother material is halogenated with a halogenating agent, and production methods in which a raw material having a halogen atom is used. In the case of the latter method, in general, such a raw material having a halogen atom is scarcely available and is expensive in many cases. Moreover, since the obtained halogenated organic pigment is a single compound, it is difficult to adjust hue and the like by controlling the number of halogen substitutions in the pigment, and thus in many cases, a halogenated organic pigment having excellent coloring properties cannot be obtained. Therefore, in general, the former methods are adopted in the industrial field.

As the former methods, (1) a method of halogenating an organic pigment using chlorine or bromine as a halogenating agent (e.g., Patent Literature 5), (2) a method of halogenating an organic pigment using N-bromosuccinimide as a halogenating agent (e.g., Patent Literature 6), and the like are known.

However, in the case of the method described in (1) above, since highly toxic chlorine or bromine is used, safety-conscious, large-scale special production equipment is required. In addition, equipment for treating a large amount of hydrogen halide gas generated as a by-product is also required. Furthermore, there has been a problem in that, due to metal elements (iron, aluminum, calcium, etc.) that have been mixed during a step of producing a pigment (in production equipment, a reaction solvent, etc.), by-products and unfavorable impurities are generated as a result of substitution or laking of a portion of a desired halogenated organic pigment with the metal elements, and are mixed into the obtained halogenated organic pigment, which adversely affect properties required for intended applications.

On the other hand, succinimide is generated as a by-product in the method described in (2) above. Thus, there have been problems such that it requires equipment for separating and removing the succinimide from the obtained halogenated organic pigment and then treating it. In addition, this method has also been problematic in that environmentally unfavorable organic solvents, such as trifluoroacetic acid or chloroform, are used in many cases, and the yield of the halogenation reaction is poor.

Furthermore, in the conventional production methods, the obtained crude halogenated organic pigment has a large particle diameter in many cases, and tends to be poor in terms of coloring properties such as coloring strength or brightness. Hence, it is difficult to directly use such a crude halogenated organic pigment as a coloring material. Thus, in many cases, in order to process the crude halogenated organic pigment into a pigment form that is highly variable as a coloring material, a pigmentation step such as acid pasting is required after the crude halogenated organic pigment is produced. However, from the viewpoint of productivity, it has been a desire to develop a method for producing a halogenated organic pigment useful as a coloring material without performing such a pigmentation step.

Meanwhile, in the case of halogenation of a common organic compound, halogenation methods in which various halogenating agents other than the aforementioned agents are used have been known. However, differing from the properties of a common organic compound, an organic pigment has poor solubility in organic solvents. Thus, it is anticipated that the halogenation reaction will hardly progress under the same reaction conditions (a solvent, a halogenating agent, etc.) as those for the halogenation reaction of a common organic compound. Accordingly, it has been desired to develop a halogenating agent that can be preferably used in halogenation of an organic pigment and a method for producing a halogenated organic pigment using the same which can solve the aforementioned problem.

PRIOR ART DOCUMENTS

Patent Literature

Patent Literature 1: Japanese Patent Laid-Open No. 2005-206630
Patent Literature 2: Japanese Patent Laid-Open No. 55-108466
Patent Literature 3: Japanese Patent Publication No. 50-4019
Patent Literature 4: Japanese Patent Laid-Open No. 56-118462
Patent Literature 5: Japanese Patent Laid-Open No. 7-292271
Patent Literature 6: National Publication of International Patent Application No. 2007-533773

Non Patent Literature

Non Patent Literature 1: Willy Herbst et al., "Industrial Organic Pigments: Production, Properties, Applications," John Wiley & Sons (1993)

SUMMARY OF INVENTION

Technical Problem

As described above, for the conventional methods for producing a halogenated organic pigment, there have been problems in terms of safety and productivity in that highly toxic raw materials such as chlorine, bromine and chloroaniline are used, the reaction yield is low, and large-scale production equipment and treatment equipment are required because a large amount of unfavorable by-products such as hydrogen halide gas and succinimide are generated as by-products. Moreover, there has also been a problem in that the obtained halogenated organic pigment has a color tone in which the adjustable range is narrow, and is difficult to prepare into fine pigment particles.

Therefore, it is an object of the present invention to provide a novel method for producing a halogenated organic pigment which is excellent in terms of safety and productivity. In addition, it is another object of the present invention to provide a halogenated organic pigment which has a wide range of color tone and is processed into fine particles, and a colored composition comprising the aforementioned halogenated organic pigment, and the like.

Solution to Problem

As a result of intensive studies directed towards achieving the aforementioned objects, the present inventors have completed the present invention.

Specifically, the present invention relates to a method for producing a halogenated organic pigment comprising a halogenation step of halogenating an organic pigment with a halogenating agent, wherein the halogenating agent comprises one or more N-haloimide compounds selected from the group consisting of trichloroisocyanuric acid, a metal salt of dichloroisocyanuric acid, tribromoisocyanuric acid, and a metal salt of dibromoisocyanuric acid.

The present invention relates to a halogenated organic pigment obtained by the above-described method for producing a halogenated organic pigment.

In addition, the present invention relates to a colored composition comprising the above-described halogenated organic pigment and a vehicle component.

Moreover, the present invention relates to color toner, inkjet ink, and color filter resist ink, each of which comprises the above-described colored composition.

The present invention relates to a printed article that is printed using the above described color toner or the above described inkjet ink.

The present invention relates to a color filter comprising a filter segment formed using the above-described color filter resist ink.

Advantageous Effects of Invention

Differing from the conventional methods for producing a halogenated organic pigment, the present invention does not use highly toxic raw materials such as chlorine, bromine or chloroaniline, but uses a highly safe and easily-handled N-haloimide compound as a halogenating agent. Thus, since the present invention does not need special production equipment, equipment for treating by-products or the like, a method for producing a halogenated organic pigment which is excellent in terms of safety, has a high total yield, and is excellent in terms of productivity can be provided.

Moreover, since a halogenated organic pigment obtained by the production method of the present invention has a color tone the adjustable range of which is wide, a colored composition which can be used for a wide range of applications and is excellent in terms of usefulness can be provided.

In the conventional production methods, in order to utilize a halogenated organic pigment as a coloring material, two-stage production steps, namely, a halogenation step and a pigmentation step, need to be carried out. In contrast, in the production method of the present invention, halogenation and pigmentation using an acid pasting treatment can be simultaneously carried out, which enables to reduce the production steps, and a method for producing a halogenated organic pigment excellent in terms of productivity can thus be provided.

DESCRIPTION OF EMBODIMENTS

The disclosure of the present applications is related to the subject matters described in Japanese Patent Application No. 2013-162396 filed on Aug. 5, 2013, and Japanese Patent Application No. 2014-60231 filed on Mar. 24, 2014, the disclosures thereof are incorporated herein by reference.

The present invention relates to a method for producing a halogenated organic pigment, wherein the method comprises a halogenation step of halogenating an organic pigment with a halogenating agent, and the halogenating agent comprises one or more N-haloimide compounds selected from the group consisting of trichloroisocyanuric acid, a metal salt of dichloroisocyanuric acid, tribromoisocyanuric acid, and a metal salt of dibromoisocyanuric acid.

The above-described N-haloimide compound more preferably comprises one or more N-chloroimide compounds selected from the group consisting of trichloroisocyanuric acid and sodium dichloroisocyanurate.

It is preferable that the above-described halogenation step be carried out in the presence of a solvent, and that the solvent comprise at least one of a strong acid and a eutectic salt.

The above described strong acid preferably comprises one or more selected from the group consisting of sulfuric acid, fuming sulfuric acid, chlorosulfonic acid, polyphosphoric acid, and methanesulfonic acid.

The above-described eutectic salt is preferably a eutectic salt of aluminum chloride and sodium chloride.

The above-described organic pigment preferably comprises at least one selected from the group consisting of a quinacridone pigment, a phthalocyanine pigment, an anthraquinone pigment, a quinophthalone pigment, a perylene pigment, an isoindolinone pigment, a dioxazine pigment, and an indanthrone pigment.

Hereinafter, the present invention will be described in detail. The term "C. I." used herein means color index.

<N-Haloimide Compound as a Halogenating Agent>

The halogenating agent used in the present invention comprises one or more N-haloimide compounds selected from the group consisting of trichloroisocyanuric acid, a metal salt of dichloroisocyanuric acid, tribromoisocyanuric acid, and a metal salt of dibromoisocyanuric acid.

The halogenation reaction in which such an N-haloimide compound is used is advantageous in that it is highly safe because the highly toxic chlorine or bromine is not used, and harmful hydrogen halide gas is not generated as a by-product during the reaction. Among the above-mentioned compounds, an N-chloroimide compound used in a chlorination reaction has been broadly used as a disinfectant for pool water, etc., and thus, it can be said that the N-chloroimide compound is an easily-handled and highly safe compound.

The above-described metal salt such as the N-haloimide compound is not particularly limited. From the viewpoint of cost and availability, an alkali metal salt is preferable, a sodium salt or a potassium salt is more preferable, and a sodium salt is particularly preferable. Accordingly, a more preferred embodiment of the halogenating agent used in the present invention includes an embodiment comprising one or more N-haloimide compounds selected from the group consisting of trichloroisocyanuric acid, sodium dichloroisocyanurate, tribromoisocyanuric acid, and sodium dibromoisocyanurate. Moreover, among halogenated organic pigments, a chlorinated organic pigment is an important compound that has been widely used in the industry. Therefore, a particularly preferred embodiment includes an embodiment comprising one or more N-chloroimide compounds selected from the group consisting of trichloroisocyanuric acid and sodium dichloroisocyanurate used as chlorinating agents.

The amount of an N-haloimide compound to be used is preferably from 1 to 2 molar equivalents of a theoretical amount based on the desired number of halogen substitutions, with respect to the amount of an organic pigment. However, the amount of an N-haloimide compound to be used can be reduced to a 1 to 1.2 molar equivalent of the theoretical amount by appropriately adjusting reaction conditions such as a reaction temperature, and the addition of a catalyst.

That is to say, the amount of an N-haloimide compound to be used is preferably from 1 to 2 molar equivalents, based on available halogen atoms.

<Solvent>

In the production method of the present invention, the halogenation step is preferably performed in the presence of a solvent. The type of such a solvent is not particularly limited as long as it does not inhibit a halogenation reaction and is not likely to cause decomposition of the structure of the organic pigment. From the viewpoint of reaction yield and the like, it is preferable to use a solvent comprising at least one of a strong acid and a eutectic salt. Examples of such a strong acid include: inorganic acids such as sulfuric acid, fuming sulfuric acid, chlorosulfonic acid, and polyphosphoric acid; and organic acids such as trifluoroacetic acid, dichloroacetic acid, methanesulfonic acid, and ethanesulfonic acid. These acids can be used as strong acids alone or as a mixture thereof. From the viewpoint of cost, reaction yield, advantages in terms of production step, or the like, inorganic acids, methanesulfonic acid, and the like are preferable, and sulfuric acid, fuming sulfuric acid, chlorosulfonic acid, polyphosphoric acid, methanesulfonic acid, and a mixture thereof are more preferable. Since sulfuric acid is likely to cause decomposition of the structure of an organic pigment when it has a high water content, high-concentration sulfuric acid (90% by mass or more) is preferable.

Examples of the eutectic salt include eutectic salt of aluminum chloride and sodium chloride.

The solvent may be a mixture of the strong acid and the eutectic salt.

The amount of a solvent is not particularly limited. When a strong acid is used as a solvent, the strong acid is used preferably in an amount of 2 to 50 mass times of the organic pigment. From the viewpoint of the solubility of the organic pigment, the number of halogen atoms substitution to be halogenated, and industrial economy, the strong acid is used more preferably in an amount of 3 to 20 mass times of the organic pigment.

When a eutectic salt is used as a solvent, it is used preferably in an amount of 2 to 30 mass times of the organic pigment.

<Organic Pigment>

The organic pigment that can be used as a raw material in the production method of the present invention is not particularly limited as long as it is an organic pigment that can be halogenated with the N-haloimide compound used in the present invention. Examples of the organic pigment used in the present invention include a quinacridone pigment, an azo pigment, a phthalocyanine pigment, an anthraquinone pigment, a dioxazine pigment, a diketopyrrolopyrrole pigment, a quinophthalone pigment, an anthrapyrimidine pigment, an anthanthrone pigment, an isoviolanthrone pigment, an indanthrone pigment, a flavanthrone pigment, a perinone pigment, a perylene pigment, an isoindoline pigment, an isoindolinone pigment, a thiazine indigo pigment, a thioindigo pigment, and a pyranthrone pigment. These organic pigments may already have a halogen as a substituent in the structure thereof as long as it has at least one hydrogen atom to be substituted with a halogen. Among these organic pigments, those comprising at least one selected from the group consisting of a quinacridone pigment, a phthalocyanine pigment, an anthraquinone pigment, a quinophthalone pigment, a perylene pigment, an isoindolinone pigment, a dioxazine pigment, and an indanthrone pigment are preferable.

The quinacridone pigment used as a raw material in the production method of the present invention is preferably a quinacridone compound represented by the following Formula I:

[Formula 1]

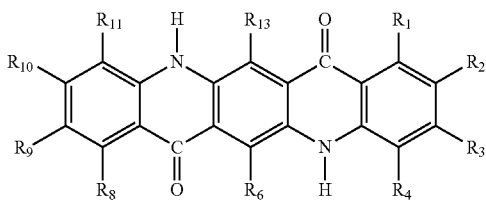

Formula 1 wherein $R_1$ to $R_4$, $R_6$, $R_8$ to $R_{11}$, and $R_{13}$ each independently represent any one selected from the group consisting of a hydrogen atom, a chlorine atom, a bromine atom, a C1-C4 alkyl group (wherein C indicates the number of carbon atoms), a C1-C4 alkoxy group, a phthalimidomethyl group, —CH$_2$NHCOCH$_2$Cl, —SO$_2$Cl, —SO$_3$M, and —X1-X2-N(X3)$_2$; M represents a hydrogen atom or an alkali metal; X1 represents —SO$_2$NH— or —CH$_2$NHCOCH$_2$NH—; X2 represents a C1-C4 alkylene group; X3 represents a C1-C4 alkyl group optionally having a heteroatom, wherein X3 groups may be connected to each other to form a ring; and at least one of $R_1$ to $R_4$, $R_6$, $R_8$ to $R_{11}$, and $R_{13}$ is a hydrogen atom.

Examples of the C1-C4 alkyl group used herein include a methyl group, an ethyl group, a propyl group, an isopropyl group, a butyl group, an isobutyl group, a sec-butyl group, and a tert-butyl group. Examples of the C1-C4 alkoxy group include a methoxy group, an ethoxy group, a propoxy group, an isopropoxy group, a butoxy group, an isobutoxy group, a sec-butoxy group, and a tert-butoxy group. M represents a hydrogen atom or an alkali metal, and examples of the alkali metal include lithium, sodium, and potassium. Examples of the C1-C4 alkylene group include a methylene group, an ethylene group, an ethylidene group, a trimethylene group, a propylene group, an isopropylidene group, a tetramethylene group, and a 2-methyl-1,3-propanediyl group. In addition, the phthalimidomethyl group means a group represented by the following (Formula II):

[Formula 2]

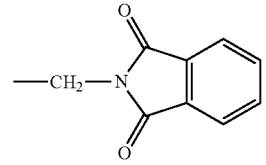

Formula 2

Examples of the heteroatom include a nitrogen atom, an oxygen atom, and a sulfur atom. As such, examples of the C1-C4 alkyl group optionally having a heteroatom include a dimethylaminomethyl group, a dimethylaminoethyl group, a methoxymethyl group, an ethoxyethyl group, a methylthiomethyl group, as well as the above-described C1-C4 alkyl groups. Furthermore, the X3 groups may be connected with each other to form a ring. In this case, since a nitrogen atom binds to the X3, the portion represented by —N(X3)$_2$ in the Formula I has the structure of a cyclic amino group. When the X3 groups are connected with each other to form a ring, examples of the formed ring include a pyrrolidine ring, a piperidine ring, a piperazine ring, a morpholine ring, and a thiazolidine ring.

Accordingly, examples of the portion represented by —N(X3)$_2$ in the Formula I include a piperidino group and a morpholino group.

A preferred embodiment of the quinacridone compound represented by the above Formula I includes a quinacridone compound wherein any one or two of $R_2$, $R_3$, $R_9$ and $R_{10}$ are atoms other than hydrogen atoms, or substituents, and other $R_1$ to $R_4$, $R_6$, $R_8$ to $R_{11}$ and $R_{13}$ are all hydrogen atoms. Herein, when any two of $R_2$, $R_3$, $R_9$ and $R_{10}$ are atoms other than hydrogen atoms, or substituents, a more preferred embodiment is a quinacridone compound wherein $R_2$ and $R_9$, or $R_3$ and $R_{10}$ are atoms other than hydrogen atoms or substituents, and other $R_1$ to $R_4$, $R_6$, $R_8$ to $R_{11}$, and $R_{13}$ are all hydrogen atoms. In particular, a particularly preferred embodiment is a quinacridone compound wherein $R_2$ and $R_9$, or $R_3$ and $R_{10}$ are each selected from the group consisting of a chlorine atom, a bromine atom, a C1-C4 alkyl group and a C1-C4 alkoxy group, and other $R_1$ to $R_4$, $R_6$, $R_8$ to $R_{11}$, and $R_{13}$ are all hydrogen atoms. Examples of such a quinacridone compound include: dialkylquinacridones such as 2,9-dimethylquinacridone (C. I. Pigment Red 122) and 2,9-diethylquinacridone; dialkoxyquinacridones such as 2,9-dimethoxyquinacridone; and dichloroquinacridones such as 2,9-dichloroquinacridone (C. I. Pigment Red 202) and 3,10-dichloroquinacridone (C. I. Pigment Red 209). Moreover, a case where $R_1$ to $R_4$, $R_6$, $R_8$ to $R_{11}$, and $R_{13}$ are all hydrogen atoms is also a particularly preferred embodiment.

In the method for producing a halogenated organic pigment of the present invention, at least one hydrogen atom represented by $R_1$ to $R_4$, $R_6$, $R_8$ to $R_{11}$ or $R_{13}$ in the quinacridone compound represented by the above Formula I can be substituted with a halogen atom. Since the present invention provides an extremely high reaction yield, it can be applied to various quinacridone compounds represented by the Formula I. Among them, it is industrially highly advantageous and preferable to use, as a raw material, an unsubstituted quinacridone wherein $R_1$ to $R_4$, $R_6$, $R_8$ to $R_{11}$ and $R_{13}$ are all hydrogen atoms which is highly distributed to the market.

Hereinafter, specific examples of organic pigments other than the quinacridone pigment, which is used as a raw material in the method for producing a halogenated organic pigment of the present invention, will be given. However, examples of organic pigments other than the quinacridone pigment are not necessarily limited thereto.

Examples of the azo pigment: C. I. Pigment Yellow 12, C. I. Pigment Yellow 83, C. I. Pigment Yellow 180, C. I. Pigment Red 146, C. I. Pigment Red 269, etc.

Examples of the phthalocyanine pigment: C. I. Pigment Red 15, C. I. Pigment Blue 15:1, C. I. Pigment Blue 15:2, C. I. Pigment Blue 15:3, C. I. Pigment Green 58, aluminum phthalocyanine, etc.

Examples of the anthraquinone pigment: C. I. Pigment Yellow 147, etc.

Examples of the dioxazine pigment: C. I. Pigment Violet 23, C. I. Pigment Violet 37, etc.

Examples of the diketopyrrolopyrrole pigment: C. I. Pigment Red 254, etc.

Examples of the quinophthalone pigment: C. I. Pigment Yellow 138, etc.

Examples of the anthrapyrimidine pigment: C. I. Pigment Yellow 108, etc.

Examples of the anthanthrone pigment: C. I. Pigment Red 168, etc.

Examples of the isoviolanthrone pigment: C. I. Pigment Violet 31, etc.

Examples of the indanthrone pigment: C. I. Pigment Blue 60, etc.

Examples of the flavanthrone pigment: C. I. Pigment Yellow 24, etc.

Examples of the perinone pigment: C. I. Pigment Orange 43, etc.

Examples of the perylene pigment: C. I. Pigment Red 178, etc.

Examples of the isoindoline pigment: C. I. Pigment Yellow 139, etc.

Examples of the isoindolinone pigment: C. I. Pigment Yellow 109, C. I. Pigment Yellow 110, etc.

Examples of the thiazine indigo pigment: C. I. Pigment Red 279 and C. I. Pigment Orange 80

Examples of the thioindigo pigment: C. I. Pigment Red 88, etc.

Examples of the pyranthrone pigment: C. I. Pigment Orange 40, etc.

<Halogenated Organic Pigment>

The halogenated organic pigment in the present invention is an organic pigment in which some substituents of the above-described pigment are substituted with halogen atoms, or an organic pigment which has halogen atoms as substituents in the basic structure thereof. Examples of the halogen include at least one of bromine and chlorine.

Specific examples of the halogenated organic pigment in the present invention include:

quinacridone pigments such as C. I. Pigment Red 202 or C. I. Pigment Red 209;

phthalocyanine pigments such as C. I. Pigment Green 7, C. I. Pigment Green 36, C. I. Pigment Blue 15:1, or C. I. Pigment Blue 15:2;

dioxazine pigments such as C. I. Pigment Violet 23;

diketopyrrolopyrrole pigments such as C. I. Pigment Red 254;

quinophthalone pigment such as C. I. Pigment Yellow 138;

anthanthrone pigments such as C. I. Pigment Red 168;

isoviolanthrone pigments such as C. I. Pigment Violet 31;

indanthrone pigments such as C. I. Pigment Blue 64;

isoindoline pigments such as C. I. Pigment Orange 66;

isoindolinone pigments such as C. I. Pigment Yellow 109, C. I. Pigment Yellow 110, or C. I. Pigment Orange 61;

thiazine indigo pigments such as C. I. Pigment Red 279;

thioindigo pigments such as C. I. Pigment Red 88 or C. I. Pigment Red 181; and pyranthrone pigments such as C. I. Pigment Orange 51, C. I. Pigment Red 216, or C. I. Pigment Red 226. In addition, compounds formed by further halogenation of these pigments are also included. However, examples of the halogenated organic pigment in the present invention are not necessarily limited thereto.

<Halogenation Step>

Reaction temperature of halogenation in the halogenation step of the production method of the present invention is preferably a temperature at which the decomposition reaction of the organic pigment used and side reactions such as a sulfonation reaction and a chlorosulfonation reaction can be suppressed. However, in the production method of the present invention, in a case where a sulfonium group, a chlorosulfonium group or the like are to be introduced into a targeted product, at least one of sulfonation and chlorosulfonation may be carried out simultaneously with halogenation on the organic pigment as a raw material.

The reaction temperature applied to halogenation can be determined, as appropriate, depending on the types of an organic pigment, a solvent and an N-haloimide compound, the presence or absence of a catalyst, and the number of halogen substitutions desired. It is generally from 0° C. to 150° C., and preferably from 10° C. to 100° C.

Since the reaction time applied to halogenation is influenced by the dissolution rate of the N-haloimide compound into a solvent, it can be determined, as appropriate, depending on the size of particles of the N-haloimide compound and the rate of stirring the reaction solution in a reaction tank. When the particle size of the N-haloimide compound is several millimeters and the stirring operation is sufficiently carried out, the reaction time is preferably from 30 minutes to 10 hours, and more preferably from 1 hour to 5 hours.

When sulfuric acid and/or chlorosulfonic acid are used as solvents, if the reaction temperature is set at high, sulfonation (in the case of using sulfuric acid) and/or chlorosulfonation (in the case of using chlorosulfonic acid) tend to occur at the same time as halogenation.

For example, when a phthalocyanine pigment is used as a raw material and sulfonation and halogenation are to be carried out, the two reactions may be carried out simultaneously by setting the reaction temperature at high, as described above. Otherwise, the reactions can be carried out in two stages, namely, the raw material is first mixed with 5% fuming sulfuric acid, and the obtained mixture is then subjected to a sulfonation treatment at a reaction temperature of 100° C. to 120° C. for 2 to 3 hours, and thereafter, the reaction temperature is decreased from that applied during the sulfonation treatment, and a halogenating agent is then added to the reaction mixture, and a halogenation treatment is performed preferably at a reaction temperature of 10° C. to 20° C. for 3 to 4 hours.

In the production method of the present invention, during the halogenation reaction, a catalyst can be added to the reaction mixture in order to improve the reaction rate. When the desired number of halogen substitutions is large, in particular, when three or more halogen atoms are substituted, the reaction yield is improved by addition of a catalyst. Examples of such a catalyst include: sulfur compounds such as sulfur or disulfur dichloride; iodine compounds such as iodine, iodine chloride, or iodine bromide; and metal chlorides such as ferric chloride, copper (I) chloride, copper (II) chloride, aluminum chloride, or antimony chloride.

The halogenated organic pigment obtained by the present invention is a mixture of a plurality of halogenated organic pigments each having a different number of halogen substitutions. For instance, an unhalogenated organic pigment is halogenated as such that the average number of halogen substitutions can be 2, and the obtained reaction product is then subjected to mass spectrometry such as TOF-MS. As a result, molecular ion peaks which correspond to halogenated organic pigments, each having the number of halogen substitutions of 1, 2 and 3, are detected in many cases, and the content ratio calculated from the peak intensities in mass spectra is approximately 1:2:1 (molar ratio). Taking a chlorinated organic pigment as an example, when the chlorinated organic pigment obtained by the present invention is compared with an organic pigment obtained by the conventional production method having the same average number of chlorine substitutions as that of the present chlorinated organic pigment which is 2, the hues of the two pigments are close to each other, but the chlorinated organic pigment obtained by the present invention is advantageous in that it is more excellent in terms of brightness and coloring strength. Specifically, although the halogenated organic pigment having the number of halogen substitutions which is 2 consists of a single component, the chlorinated organic pigment obtained by the present invention is a mixture of three components, which are organic pigments each having the number of chlorine substitutions of 1, 2 and 3 (approximately 1:2:1 (molar ratio)). As a result, it is assumed that crystallinity of the chlorinated organic pigment of the present invention is reduced and fine pigment particles are formed, and excellent color tone is thereby produced.

Moreover, the halogenated organic pigment obtained by the present invention can be adjusted to have a wide range of color tone by varying the number of halogen substitutions. If hydrogen atoms in an organic pigment are substituted with halogen atoms, it results in an increase in wavelength of visible absorption in many cases. Accordingly, the color becomes deeper as the number of halogen substitutions increases. For example, when approximately 8 chlorine atoms are introduced into an unsubstituted quinacridone, the halogenated quinacridone obtained by the present invention has a maroon color.

Also, by incorporating the production method of the present invention, productivity of the conventional method for producing a quinacridone can be further improved. For example, an isolation operation of an unsubstituted quinacridone becomes unnecessary by synthesizing an unsubstituted quinacridone by ring-closing 2,5-dianilinoterephthalic acid with polyphosphoric acid, and then using the reaction solution for carrying out the halogenation reaction according to the present invention. Furthermore, since both the ring-closing reaction and the halogenation reaction can be continuously carried out using polyphosphoric acid as a solvent, excellent productivity can be achieved. Further, the aforementioned dichloroquinacridone sodium sulfonate disclosed as a dispersion aid can be obtained by sulfonation of dichloroquinacridone. When sulfuric acid is used as a solvent in the production method of the present invention, both the chlorination reaction and the sulfonation reaction can be simultaneously carried out, which enables a single step production.

Since the production method of the present invention does not use the raw materials used in the conventional methods such as chloroaniline that is suspected of being carcinogenic, or highly toxic chlorine gas or bromine gas, it is, obviously, excellent in terms of safety. For example, chloroaniline is obtained by a chlorination reaction of chlorinating benzene with chlorine gas, a nitration reaction, and a reduction reaction. However, these reactions can involve risks or disadvantages on the production process such as the use of highly toxic chlorine gas, and the need for treatment of a large amount of hydrogen chloride gas generated as a by-product. In contrast, the production method of the present invention, which does not generate harmful hydrogen halide gas as a by-product, is advantageous in that it has high safety, and does not need a large-scale treatment apparatus.

In comparison to the conventional methods, the production method of the present invention has a high reaction yield and is excellent in terms of productivity. For example, in the case of a conventional method of producing a chlorinated quinacridone using chloroaniline as a starting raw material, the production conditions have influence on the reaction yield. According to the findings by the present inventors, the reaction yield is approximately 80% under standard production conditions. In contrast, in the case of the production method of the present invention, the reaction yield would be approximately 90% when estimated from a production process of producing a chlorinated quinacridone via an unsubstituted quinacridone, using aniline as a starting raw material.

The halogenated organic pigment obtained by the production method of the present invention preferably satisfies at least one of the following (1) to (3). By satisfying any one of these conditions, the obtained halogenated pigment can have, as a coloring material, coloring properties such as coloring strength and brightness, and durability such as lightfastness, heat resistance, and migration resistance.

(1) The average number of halogen substitutions is 0.05 or more and 7.0 or less.
(2) The halogen distribution width is 3 or more.
(3) The average particle diameter is 0.1 µm or less, and preferably 0.06 µm or less. The measurement of the average particle diameter will be described later.

In the cases where the obtained halogenated organic pigment is a phthalocyanine pigment, it is preferable that at least one of the aforementioned conditions (1) to (3) and the following conditions (4) and (5) is satisfied.

(4) The content of aluminum phthalocyanine and halogenated aluminum phthalocyanine is 1.0% by mass or less.

(5) The central element is any one or more selected from the group consisting of hydrogen, manganese, iron, cobalt, zinc, nickel, and copper.

The production method of the present invention has excellent productivity also for a solid solution pigment comprising a halogenated organic pigment. In the conventional method of preparing a solid solution pigment, for example, an unhalogenated organic pigment and a halogenated organic pigment are dissolved in an organic solvent comprising sulfuric acid or a strong base, and are uniformly mixed. Thereafter, a poor solvent, a neutralizer and the like are added to the mixture for precipitation and isolation. Thereafter, as necessary, the resultant is dissolved in a solvent to prepare slurry, and then subjected to a heat treatment, or added with an inorganic salt, polyhydric alcohol and the like to perform pigmentation by solvent salt milling. In contrast, in the production method of the present invention, a solid solution pigment having the same color tone as described above can be obtained by the following steps, for example: when an organic pigment used as a raw material is halogenated using sulfuric acid as a solvent, the amount of an N-haloimide compound to be added is set at slightly smaller than that of the raw material, so that a portion of the raw material can be halogenated, and the remaining raw material cannot be halogenated. Hence, the production method of the present invention makes it possible to simultaneously carry out a halogenation reaction and preparation of a solid solution pigment.

<Pigmentation>

Since halogenation and pigmentation by an acid pasting treatment are simultaneously carried out in the production method of the present invention, a reduction in the production steps can be achieved, and also, a halogenated organic pigment that is in a pigment form with high use value can be obtained. However, the present production method may further comprise another pigmentation step (which is also referred to as a conditioning or finishing step) for finishing the pigment to a desired pigment form depending on the intended use of the pigment as a coloring material.

When such a pigmentation step is carried out, it is preferable to carry out, after completion of the halogenation step, a separation step of distilling the solvent away from the reaction solution, or diluting the reaction solution with a large amount of water, so that the halogenated organic pigment is precipitated, then filtrating it, and separating it as an aqueous cake or a dry product of the halogenated organic pigment, and thereafter, carry out a known pigmentation step. Examples of the treatment in such a known pigmentation step include a heat treatment in the presence of an organic solvent, a solvent salt milling treatment involving addition of inorganic salt and polyhydric alcohol, and an acid pasting treatment involving dissolution of the pigment in sulfuric acid or the like and the subsequent dilution with a large amount of water. Moreover, during, before or after the pigmentation step, a resin, a surfactant, an extender pigment, a pigment dispersant and the like may be added, so that the use value of the pigment may be enhanced. Herein, the term "pigment dispersant" is a generic term for compounds having an ability to disperse pigments, and indicates a compound in which an acidic substituent, a basic substituent or the like are introduced into the pigment structure, and a high molecular weight compound having a partial structure that largely interacts with a pigment in a molecule, and the like.

As described above, the method for producing a halogenated organic pigment of the present invention is a method excellent in terms of safety and productivity.

<Colored Composition and Application Thereof>

The halogenated organic pigment obtained by the production method of the present invention, which is mixed with a vehicle component to prepare a colored composition, can be preferably used as a coloring material for printing ink, a coating material, a plastic colorant, a textile printing agent, color toner, inkjet ink, color filter resist ink, and the like. In particular, the present colored composition can be preferably used for a plastic colorant, color toner, inkjet ink, color filter resist ink, and the like.

Since the halogenated organic pigment obtained by the production method of the present invention has a wide range of color tone and can be finely dispersed, it can be used as a colored composition for color toner, inkjet ink, color filter resist ink, and the like, thereby providing final products exhibiting excellent brightness and high coloring strength, such as a printed article, a coated product, or a color filter.

The colored composition of the present invention comprises the halogenated organic pigment obtained by the production method of the present invention and a vehicle component. The colored composition is formed by mixing the present halogenated organic pigment with a vehicle component, then dispersing the halogenated organic pigment using a dispersing device such as a ball mill, a bead mill, a roll mill, or a high-speed impact mill, then adding as necessary various additives such as a dispersant, color tone adjusting material, physical property adjusting material, and then blending them. The content of the halogenated organic pigment in the colored composition is preferably in the range of 0.1% by mass to 80% by mass. Moreover, the content of the vehicle component in the colored composition is preferably in the range of 20% by mass to 99.9% by mass.

Examples of the vehicle component used in the colored composition include a vehicle for offset ink, a vehicle for gravure ink, a vehicle for coating materials, a vehicle used for plastic colorants, a vehicle for textile printing, a resin for color toners, a vehicle for inkjet ink, and a vehicle for color filter resist ink.

The vehicle for offset ink consists of, for example: a resin such as a rosin modified phenolic resin, a petroleum resin, an alkyd resin, or a dry oil modified resin thereof; and as necessary, vegetable oil such as flaxseed oil, wood oil or soybean oil; and a solvent such as n-paraffin, isoparaffin, aromatic, naphthene or α-olefin. The mixing ratio of these components is preferably in the range of the resin: the vegetable oil: the solvent=10% to 50% by mass: 0% to 30% by mass: 20% to 60% by mass, based on the total mass of the vehicle component (100% by mass).

As necessary, known additives such as ink solvent, a dryer, a leveling improver, and a thickener can be appropriately mixed into the offset ink.

The vehicle for gravure ink consists of a resin and a solvent. The mixing ratio of these components is preferably in the range of the resin: the solvent=5% to 40% by mass: 60% to 95% by mass, based on the total mass of the vehicle component (100% by mass).

Examples of the resin include gum rosin, wood rosin, tall oil rosin, lime rosin, rosin ester, maleic acid resin, gilsonite, dammar, shellac, polyamide resin, vinyl resin, nitrocellulose, cyclized rubber, chlorinated rubber, ethyl cellulose, cellulose acetate, ethylene-vinyl acetate copolymer resin, urethane resin, polyester resin, and alkyd resin.

Examples of the solvent include: aliphatic hydrocarbons such as n-hexane; aromatic hydrocarbons such as toluene; alcohols such as methanol, ethanol, or isopropyl alcohol; ketones such as acetone or methyl ethyl ketone; esters such as ethyl acetate, or ethyl lactate, ethyl acetoacetate; ethers such as diethyl ether; ether alcohols such as ethylene glycol monoethyl ether, ethylene glycol monomethyl ether, or ethylene glycol monobutyl ether; and aromatic halides such as chlorbenzol.

As necessary, known additives, including extender pigments such as barium sulfate, barium carbonate, calcium carbonate, calcium sulfate, alumina white, clay, silica, silica white, talc, calcium silicate or precipitated magnesium carbonate, and also, auxiliary agents such as a pigment dispersant, a plasticizer, an ultraviolet inhibitor, an antioxidant or an antistatic agent, can be appropriately mixed into the gravure ink.

The vehicle for coating materials consists of a resin and a solvent. The mixing ratio of these components is preferably in the range of the resin: the solvent=5% to 45% by mass: 55 to 95% by mass, based on the total mass of the vehicle component (100% by mass).

Examples of the resin include nitrocellulose, aminoalkyd resin, acrylic resin, aminoacrylic resin, urethane resin, polyvinyl acetal resin, epoxy resin, polyester resin, polyvinyl chloride resin, vinylidene fluoride resin, vinyl fluoride resin, and polyethersulfone resin.

Examples of the solvent include organic solvents such as aliphatic hydrocarbons, aromatic hydrocarbons, halogenated hydrocarbons, alcohols, ketones, esters, ethers, ether alcohols or ether esters, and water.

As necessary, known additives such as an extender pigment, a pigment dispersant, a leveling improver, a thickener, or a curing agent can be appropriately mixed into the coating material.

Examples of the vehicle used for plastic colorants include aromatic carboxylic acid, aliphatic carboxylic acid aromatic carboxylic acid metal salt, aliphatic carboxylic acid metal salt, aliphatic carboxylic acid ester, polyethylene wax, low density polyethylene (LDPE), and high density polyethylene (HDPE).

A plastic material is colored with a plastic colorant and/or the halogenated organic pigment of the present invention, and then, can be molded into a colored plastic. Examples of a plastic resin used for plastic molding include: polyolefin resins such as polypropylene resin, polyethylene resin, ethylene-propylene copolymer, copolymer of α-olefin and acrylic acid or maleic acid, ethylene-vinyl acetate copolymer, or copolymer of ethylene and acrylic acid or maleic anhydride; vinyl resins such as polyvinyl chloride resin or polyvinyl acetate; acetal resins such as formal resin or butyral resin; acrylic resins such as polyacrylonitrile or methacryl resin; styrol resins such as polystyrene or acrylonitrile-butadiene-styrene copolymer; polyester resins such as polyethylene terephthalate or polycarbonate; nylon such as 6-nylon; unsaturated polyester resins; epoxy resins; urea resins; melamine resins; and cellulose resins. These resins can also be used as vehicles used for plastic colorants.

As necessary, known additives such as a plasticizer, an ultraviolet inhibitor, an antioxidant or a releasing agent can be appropriately mixed into the plastic colorant.

The vehicle for textile printing is a reducer, a fixing agent or the like, which is mixed into a pigment dispersion obtained by dispersing a pigment in a high concentration into a nonionic surfactant aqueous solution, an anionic surfactant aqueous solution or the like, and the vehicle for textile printing consists of a resin and a solvent. The mixing ratio thereof is preferably in the range of the resin: the solvent=1% to 20% by mass: 80% to 99% by mass, based on the total mass of the vehicle component (100% by mass).

Examples of the resin include acrylic resin, aminoacrylic resin, and urethane resin. Examples of the solvent include organic solvents such as aliphatic hydrocarbons, aromatic hydrocarbons, alcohols, ketones, esters, ethers, ether alcohols, or ether esters, and water.

As necessary, known additives such as a pigment dispersant, a defoaming agent, a thickener, or a surfactant can be appropriately mixed into the textile printing agent.

Examples of the resin for color toners include polystyrene resin, styrene-acrylic acid copolymer, polyvinyl chloride resin, styrene-vinyl acetate copolymer, rosin modified maleic acid resin, phenolic resin, epoxy resin, polyester resin, low-molecular-weight polyethylene, low-molecular-weight polypropylene, ionomer resin, polyurethane resin, silicone resin, rosin ester, and rosin.

As necessary, known additives such as a pigment dispersant, a charge control agent or a releasing agent can be appropriately mixed into the color toner.

The vehicle for inkjet ink consists of a resin and a solvent. The mixing ratio thereof is preferably in the range of the resin: the solvent=1% to 10% by mass: 90% to 99% by mass, based on the total mass of the vehicle component (100% by mass).

Examples of the resin include resins that are soluble in water, such as acrylic resin, styrene-acrylic acid copolymer, polyester resin, polyamide resin, polyurethane resin or fluorine resin; water-dispersible emulsion, and colloidal dispersion resin. To these resins, neutralizers such as ammonia, amine or inorganic alkali can be added, as necessary.

Examples of the solvent include water, ethylene glycol, polyethylene glycol, ethylene glycol monomethyl ether, and substituted pyrrolidone. In addition, for the purpose of increasing the drying property of inkjet ink, alcohols such as methanol, ethanol or isopropyl alcohol can also be used.

As necessary, known additives such as an antiseptic, a penetrant or a chelating agent, and also, for improving the dispersion stability of a pigment, an anionic surfactant, a nonionic surfactant, a cationic surfactant, an amphoteric surfactant and the like can be appropriately mixed into the inkjet ink. The inkjet ink can also be used in production of color filters.

The vehicle for color filter resist ink consists of a resin comprising at least any one selected from the group consisting of a thermoplastic resin, a thermosetting resin and an active energy ray curable resin, a monomer and/or an oligomer, and a solvent. The mixing ratio thereof is preferably in the range of the resin: the monomer and/or oligomer: the solvent=4% to 15% by mass: 2% to 8% by mass: 77% to 94% by mass, based on the total mass of the vehicle component (100% by mass).

Examples of the thermoplastic resin include butyral resin, styrene-maleic acid copolymer, chlorinated polyethylene resin, chlorinated polypropylene resin, polyvinyl chloride resin, vinyl chloride-vinyl acetate copolymer, polyvinyl acetate resin, polyurethane resin, polyester resin, acrylic resin, alkyd resin, polystyrene resin, polyamide resin, rubber resin, cyclized rubber resin, cellulose resin, polyethylene resin, polybutadiene resin, and polyimide resin. Examples of the thermosetting resin include epoxy resin, benzoguanamine resin, rosin modified maleic acid resin, rosin modified fumaric acid resin, melamine resin, urea resin, and phenolic resin. Examples of the active energy ray curable resin include a resin in which a photocrosslinking group of a (meth)acryl compound, cinnamic acid, or the like into a linear polymer having a reactive substituent such as a hydroxyl group, a carboxyl group, an amino group via an isocyanate group, an aldehyde group, an epoxy group, or the like.

Examples of the monomer and the oligomer include: various acrylic acid esters and methacrylic acid esters such as methyl (meth)acrylate, ethyl (meth)acrylate, 2-hydroxyethyl (meth)acrylate, 2-hydroxypropyl (meth)acrylate, cyclohexyl (meth)acrylate, β-carboxyethyl (meth)acrylate, polyethylene glycol di(meth)acrylate, 1,6-hexanediol di(meth)acrylate, triethylene glycol di(meth)acrylate, tripropylene glycol di(meth)acrylate, trimethylolpropane tri(meth)acrylate, pentaerythritol tri(meth)acrylate, 1,6-hexanediol diglycidyl ether di(meth)acrylate, bisphenol A diglycidyl ether di(meth)acrylate, neopentyl glycol diglycidyl ether di(meth)acrylate, dipentaerythritol hexa(meth)acrylate, tricyclodecanyl (meth)acrylate, ester acrylate, (meth)acrylic acid ester of methylol melamine, epoxy (meth)acrylate, and urethane acrylate; and (meth)acrylic acid, styrene, vinyl acetate, hydroxyethyl vinyl ether, ethylene glycol divinyl ether, pentaerythritol trivinyl ether, (meth)acrylamide, N-hydroxymethyl (meth)acrylamide, N-vinyl formamide, and acrylonitrile. These can be used alone or in combination of two or more types.

Examples of the solvent include organic solvents such as aliphatic hydrocarbons; aromatic hydrocarbons such as ethyl benzene, xylene or toluene; halogenated hydrocarbons; alcohols such as ethanol, propanol, butanol, ethylene glycol, diethylene glycol or glycerin; ketones such as cyclohexanone or methyl ethyl ketone; esters such as ethyl acetate; ethers such as diethylene glycol dimethyl ether or ethylene glycol diethyl ether; ether alcohols such as ethylene glycol monomethyl ether; and ether esters such as ethyl cellosolve acetate.

As necessary, known additives such as a pigment dispersant, a photopolymerization initiator or a sensitizer can be appropriately added to the color filter resist ink.

<Printed Article and Color Filter>

The printed article of the present invention is characterized in that it is printed using the above-described color toner or the above-described inkjet ink. The printed article of the present invention can be obtained by applying the color toner or the inkjet ink to a film or sheet substrate by a known printing method such as gravure printing or flexographic printing, and then fixing a coated film by drying in an oven.

Examples of the above-described substrate include polyolefin such as polyethylene or polypropylene, polyester such as polyethylene terephthalate, polycarbonate or polylactic acid, polystyrene resins such as polystyrene, an AS resin or an ABS resin, nylon, polyamide, polyvinyl chloride, polyvinylidene chloride, cellophane, a paper, aluminum, and composite materials thereof.

The color filter of the present invention is characterized in that it comprises a filter segment which is formed using the above-described color filter resist ink.

The color filter may comprise at least one red filter segment, at least one green filter segment, and at least one blue filter segment, and may further comprise a magenta filter segment, a cyan filter segment, and a yellow filter segment.

The color filter of the present invention can be produced by a known printing method or a photolithography method.

EXAMPLES

Hereinafter, the present invention will be described based on the following examples. However, the present invention is not limited to these examples. In the examples, "part" and "%" indicate "parts by mass" and "% by mass", respectively.

Identification of a compound was carried out based on the matching of molecular ion peaks in the mass spectrum obtained using a time-of-flight mass spectrometer (autoflexIII (TOF-MS), manufactured by Bruker Daltonics K. K.) with mass numbers obtained by calculation, and the matching of the ratio of carbon, hydrogen and nitrogen obtained using an elemental analyzer (Elemental Analyzer 2400CHN, manufactured by PerkinElmer Co., Ltd.) with the theoretical value.

The amount of halogen atoms were calculated by burning a compound by an oxygen combustion flask method, then quantifying the content of liquid absorbed by water by ion chromatography, and then converting the obtained value to the number of halogen substitutions.

In addition, with regard to the content ratio (molar ratio) of each component (halogenated compound) in the obtained halogenated organic pigment, the ratio of signal strengths (peaks) of individual components in the mass spectrum obtained by the TOF-MS measurement was defined as the molar ratio of the components.

The average particle diameter of pigment particles was measured and calculated by the following method. Propylene glycol monomethyl ether acetate was added to pigment particles, and a small amount of Disperbyk-161 (manufactured by BYK Japan) was then added as a resin-type dispersant to the particles, and the obtained mixture was then subjected to a dispersion treatment for 1 minute in a water bath of an ultrasonic washing machine to prepare a measurement sample. Using this sample, 6 photographs (6 visual fields) of the sample, in each of which 200 or more primary particles of the pigment could be observed, were taken at a magnification of 50,000 to 100,000 times by using a transmission electron microscope (TEM), and the sizes of 1000 primary particles (the minor axis diameter and major axis diameter of each particle) were arbitrarily measured in units of nm, and the average value thereof was defined as the average particle diameter of the pigment particles.

Hereafter, examples of the production method of the present invention will be given.

Example 1

99 parts of 98% sulfuric acid were mixed with 21 parts of 30% fuming sulfuric acid to prepare 120 parts of 99.5% sulfuric acid. To this sulfuric acid, 0.1 part of iodine was added as a catalyst, and thereafter, 20 parts of copper phthalocyanine (C. I. Pigment Blue 15, T-99 CRUDE BLUE, manufactured by ZHUHAI TOYOCHEM CO., LTD.) was added as a phthalocyanine pigment while keeping the temperature at 30° C. or lower and cooling in an ice bath. Subsequently, the temperature was increased to 50° C., 2.7 parts of trichloroisocyanuric acid was then added to the reaction mixture, and the obtained mixture was stirred at the same temperature as described above for 3 hours. At this time, the amount of trichloroisocyanuric acid was 0.33 times the mole of copper phthalocyanine, and was 1.00 molar equivalent based on available chlorine atoms. Subsequently, the above-described reaction solution was poured into 600 parts of water while stirring, and the obtained solution was then heated to 70° C. Thereafter, the solution was subjected to filtration, washing with hot water, washing with 1% sodium hydroxide aqueous solution, and washing with hot water in this order. Thereafter, the reaction solution was dried to obtain 18.6 parts of chlorinated copper phthalocyanine having an average number of chlorine substitutions of 0.9. The yield was 89%.

This chlorinated copper phthalocyanine was observed under an electron microscope. As a result, the average particle diameter was 0.06 μm. The halogen distribution width was 4. Aluminum phthalocyanine and chlorinated aluminum phthalocyanine were not observed.

The above-described halogen distribution width and the contents of aluminum phthalocyanine and halogenated aluminum phthalocyanine were measured as follows using a time-of-flight mass spectrometer (autoflexIII (TOF-MS), manufactured by Bruker Daltonics K. K.). The contents of aluminum phthalocyanine and halogenated aluminum phthalocyanine were obtained by calculating the signal strength (each peak value) of the molecular ion peak corresponding to each component and the value obtained by integration of individual peak values (total peak value) in the mass spectrum of a pigment obtained by performing mass spectrometry using the aforementioned device, and calculation based on the ratio of each peak value to the total peak value.

The halogen distribution width was obtained by counting the number of peaks in which the ratio of each peak value to the total peak value was 1% or more.

Examples 2 to 10

Each halogenated phthalocyanine was obtained in the same method as in Example 1 with the exception that the conditions were changed to those shown in Table 1 and Table 2. 2% Fuming sulfuric acid was prepared by mixing 86 parts of 98% sulfuric acid with 34 parts of 30% fuming sulfuric acid. The molar equivalent of the amount charged shown in Table 1 indicates the molar equivalent based on available halogen atoms. The number of chlorine substitutions, the number of bromine substitutions, and the yield of the obtained halogenated phthalocyanines are also shown in Table 2.

The used N-haloimide compounds were all granular, white solids, and were easily-handled, and no gas was generated during the reaction, and a series of operations were extremely easily carried out.

The chlorinated copper phthalocyanines obtained in Examples 2 to 10 were observed under an electron microscope. The average particle diameter of all of these compounds was 0.06 μm. Aluminum phthalocyanine and chlorinated aluminum phthalocyanine were not observed.

TABLE 1

| | Solvent | | N-haloimide compound | |
| --- | --- | --- | --- | --- |
| Example | Name | Amount charged (parts by mass) | Name | Amount charged (upper row: parts by mass) (lower row molar equivalent) |
| 2 | 2% Fuming sulfuric acid | 120 | Trichloroisocyanuric acid | 2.7 / 1.0 |
| 3 | 2% Fuming sulfuric acid | 120 | Sodium dichloroisocyanurate | 3.8 / 1.0 |
| 4 | 99.5% Sulfuric acid | 120 | Trichloroisocyanuric acid | 2.7 / 1.0 |
| 5 | Chlorosulfonic acid | 120 | Trichloroisocyanuric acid | 6.0 / 2.2 |
| 6 | Chlorosulfonic acid | 120 | Trichloroisocyanuric acid | 8.8 / 3.3 |
| 7 | Chlorosulfonic acid | 120 | Trichloroisocyanuric acid | 12.0 / 4.5 |
| 8 | Chlorosulfonic acid | 120 | Sodium dibromoisocyanurate | 10.2 / 1.9 |
| 9 | Chlorosulfonic acid | 120 | Tribromoisocyanuric acid | 9.9 / 2.3 |
| 10 | Chlorosulfonic acid | 120 | Trichloroisocyanuric acid | 2.2 / 0.8 |

TABLE 2

| | Catalyst | | Reaction temperature (° C.) | Reaction time (hr) | Yield (parts by mass) | Number of chlorine substitutions (average) | Number of bromine substitutions (average) | Yield (% by mass) |
| --- | --- | --- | --- | --- | --- | --- | --- | --- |
| Example | Name | Amount charged (parts by mass) | | | | | | |
| 2 | None | None | 30 | 4 | 19.4 | 0.9 | — | 92 |
| 3 | None | None | 30 | 4 | 18.6 | 0.9 | — | 88 |
| 4 | None | None | 50 | 3 | 17.4 | 0.7 | — | 84 |
| 5 | Iodine | 0.1 | 20 | 2 | 21.9 | 2.1 | — | 97 |
| 6 | Iodine | 0.1 | 20 | 3 | 21.6 | 3.0 | — | 89 |
| 7 | Iodine | 0.1 | 20 | 3 | 21.8 | 4.0 | — | 87 |
| 8 | Iodine | 0.3 | 30 | 3 | 21.9 | — | 1.6 | 90 |
| 9 | Iodine | 0.3 | 30 | 3 | 21.6 | — | 2.1 | 84 |
| 10 | Iodine | 0.1 | 20 | 3 | 19.9 | 0.8 | — | 95 |

COMPARATIVE EXAMPLE

An example of producing halogenated phthalocyanine using chlorine gas, which is a conventional method, will be described below.

81 parts of aluminum chloride, 19 parts of sodium chloride, and 1 part of ferric chloride were fused by heating, and thereafter, 20 parts of copper phthalocyanine (C. I. Pigment Blue 15, T-99 CRUDE BLUE, manufactured by ZHUHAI TOYOCHEM CO., LTD.) were added to the above mixture at 140° C. The temperature of the reaction mixture was increased to 160° C., and 5 parts of chlorine gas were then blown into the reaction solution. The reaction solution was poured into 1000 parts of water, and the obtained solution was then subjected to filtration, washing with hot water, washing with 1% hydrochloric acid aqueous solution, washing with hot water, washing with 1% sodium hydroxide aqueous solution, and washing with hot water in this order. Thereafter, the reaction solution was dried to obtain 20.6 parts of crude chlorinated copper phthalocyanine having an average number of chlorine substitutions of 2.0. The yield was 92%. During the blowing of chlorine gas, sublimates of hydrogen chloride gas and aluminum chloride were generated. Thus, a device for capturing these sublimates was required.

Comparative Example 2

Using the crude chlorinated copper phthalocyanine obtained in Comparative Example 1, pigmentation was performed by acid pasting. 20 parts of the crude chlorinated copper phthalocyanine were dissolved in 120 parts of 98% sulfuric acid, and the obtained mixture was then stirred at 50° C. for 3 hours. Subsequently, the solution was poured into 600 parts of water while stirring. The obtained solution was heated to 70° C., and was then subjected to filtration, washing with hot water, washing with 1% sodium hydroxide aqueous solution, and washing with hot water, and was then dried to obtain 19.2 parts of chlorinated copper phthalocyanine having an average number of chlorine substitutions of 2.0. The yield was 96%. A portion of this chlorinated copper phthalocyanine was subjected to compression molding to obtain a tablet, and it was then measured using an X-ray fluorescence analyzer and a mass spectrometer. As a result, aluminum phthalocyanine and aluminum phthalocyanine substituted with 1 to 4 chlorine atoms were detected, and the content thereof was 4.9% by mass.

Comparative Example 3

An example of producing halogenated phthalocyanine using a raw material having a halogen atom, which is a conventional method, will be described below.

28 parts of phthalic anhydride, 105 parts of chlorophthalic anhydride, 19 parts of copper (I) chloride, 139 parts of urea, 0.5 parts of ammonium molybdate, and 210 parts of tert-amylbenzene (trade name: Hisol P, alkylbenzene mixture, manufactured by Nippon Oil Co., Ltd.) as a solvent were added into a glass autoclave, and the obtained mixture was then reacted at 200° C. under a pressure of 2.0 kg/cm$^2$·G for 4 hours. Thereafter, the purified slurry was heated under a reduced pressure so that the solvent was distilled away and recovered. 2000 parts of 5% sulfuric acid were added to the residue, and thereafter, the obtained mixture was stirred at 90° C. for 4 hours and was filtrated. The resultant was dried to obtain 109.7 parts of crude chlorinated copper phthalocyanine having an average number of chlorine substitutions of 3.0. The yield was 85%.

Comparative Example 4

Using the crude chlorinated copper phthalocyanine obtained in Comparative Example 3, pigmentation was performed by acid pasting. 20 parts of the crude chlorinated copper phthalocyanine were dissolved in 120 parts of 98% sulfuric acid, and the obtained mixture was then stirred at 50° C. for 3 hours. Subsequently, the solution was poured into 600 parts of water while being stirred. The obtained solution was heated to 70° C., and was then subjected to filtration, washing with hot water, washing with 1% sodium hydroxide aqueous solution, and washing with hot water in this order. Thereafter, the reaction solution was dried to obtain 19.3 parts of chlorinated copper phthalocyanine having an average number of chlorine substitutions of 3.0. The yield was 96%.

As shown in Comparative Examples 1 to 4, in order to utilize the halogenated organic pigments obtained by the conventional production methods as coloring materials, two stages of production steps, namely, a halogenation step and a pigmentation step were required. In contrast, the halogenated organic pigment obtained by the production method of the present invention can be utilized as a coloring material without performing such a pigmentation step. Accordingly, a reduction in the production steps is possible, and thus, it can be said that the production method of the present invention is excellent in terms of productivity.

Comparative Example 5

An example of producing halogenated phthalocyanine according to the method described in Patent Literature 6 will be described below.

A mixture of 20 parts of copper phthalocyanine (C. I. Pigment Blue 15, T-99 CRUDE BLUE manufactured by ZHUHAI TOYOCHEM CO., LTD.) as a phthalocyanine pigment and 28 parts of N-bromosuccinimide was stirred in a solution of 1400 mL of trifluoroacetic acid and 420 mL of 98% sulfuric acid at a room temperature for 24 hours. At this time, the amount of N-bromosuccinimide was 4.52 times the mole of copper phthalocyanine, and was 4.52 molar equivalents based on available bromine atoms. The obtained dark blue solution was poured into 5000 parts of ice water. The obtained solid was washed with water, was then collected by filtration, and was then dried to obtain 17.5 parts of brominated copper phthalocyanine. The yield was 58%, which was lower than those of Examples 7 and 8 in which bromination was also carried out. In addition, the average number of bromine substitutions was 3.76, which is lower than the theoretically obtained number of bromine substitutions.

Example 11

10 parts of C. I. Pigment Yellow 147 (Filestar Yellow RNB, manufactured by BASF) which is an anthraquinone pigment was added to and was dissolved in 150 parts of chlorosulfonic acid, and thereafter, 2.6 parts of trichloroisocyanuric acid were added to the solution. The obtained mixture was stirred at 20° C. for 2 hours. At this time, the amount of trichloroisocyanuric acid was 0.66 times the mole of Pigment Yellow 147, and was 2.0 molar equivalents based on available chlorine atoms. Subsequently, the reaction solution was poured into 600 parts of water while being stirred. The obtained solution was heated to 70° C., and was then subjected to filtration, washing with hot water, washing with 1% sodium hydroxide aqueous solution, and washing with hot water in this order. Thereafter, the resultant was dried to obtain 10.8 parts of chlorinated Pigment Yellow 147 having an average number of chlorine substitutions of 1.9. The yield was 97%.

Comparative Example 6

An example of a production method using chlorine gas will be described below as a conventional technique.

A halogenation reaction was carried out in the same manner as that of Example 11 with the exception that chlorine gas was used instead of the trichloroisocyanuric acid of Example 11. The chlorine gas was introduced into the bottom part of the reaction solution through a glass tube at a rate of approximately 2 parts/hour until the number of chlorine substitutions became 2.0. The total amount of chlorine gas introduced was 6.1 parts. When the number of chlorine substitutions is 2.0, the theoretical amount of chlorine gas that is necessary is 3.2 parts, which means that the yield based on chlorine gas was 52%. Moreover, the yield of the halogenated compound was 10.3 parts and the yield was 92%, which were lower than those of Example 11. Furthermore, in order to capture unreacted chlorine gas and hydrogen chloride gas generated as a by-product, a device for allowing alkaline water to absorb these gases was also needed in addition to the production device of Example 11.

Example 12

10 parts of C. I. Pigment Yellow 138 (Paliotol Yellow K0961HDK, manufactured by BASF) which is a quinophthalone pigment was added to and was dissolved in 80 parts of chlorosulfonic acid, and thereafter, 1.1 parts of trichloroisocyanuric acid were added to the solution. The obtained mixture was stirred at 10° C. for 3 hours. At this time, the amount of trichloroisocyanuric acid was 0.33 times the mole of Pigment Yellow 138, and was 1.00 molar equivalent based on available chlorine atoms. Subsequently, the reaction solution was poured into 600 parts of water while being stirred. The obtained solution was heated to 70° C., and was then subjected to filtration, washing with hot water, washing with 1% sodium hydroxide aqueous solution, and washing with hot water in this order. Thereafter, the resultant was dried to obtain 9.6 parts of chlorinated Pigment Yellow 138 having an average number of chlorine atoms, which were further substituted, of 0.3. The yield was 94%. The average number of chlorine substitutions (total) was 8.3. The average particle diameter was 0.06 μm.

Example 13

10 parts of C. I. Pigment Red 178 (Paliogen Red K3911, manufactured by BASF) which is a perylene pigment was added to and was dissolved in 80 parts of 98% sulfuric acid, and thereafter, 1.04 parts of trichloroisocyanuric acid were added to the solution. The obtained mixture was stirred at 10° C. for 3 hours. At this time, the amount of trichloroisocyanuric acid was 0.33 times the mole of Pigment Red 178, and was 1.00 molar equivalent based on available chlorine atoms. Subsequently, the reaction solution was poured into 600 parts of water while being stirred. The obtained solution was heated to 70° C., and was then subjected to filtration, washing with hot water, washing with 1% sodium hydroxide aqueous solution, and washing with hot water in this order. Thereafter, the resultant was dried to obtain 9.9 parts of chlorinated Pigment Red 178 having an average number of chlorine substitutions of 1.00. The yield was 98%. The average particle diameter was 0.05 μm.

Example 14

10 parts of C. I. Pigment Yellow 109 (Irgazin Yellow L1030, manufactured by BASF) which is an isoindolinone pigment was added to and was dissolved in 80 parts of chlorosulfonic acid, and thereafter, 1.19 parts of trichloroisocyanuric acid were added to the solution. The obtained mixture was stirred at 10° C. for 3 hours. At this time, the amount of trichloroisocyanuric acid was 0.33 times the mole of Pigment Yellow 109, and was 1.00 molar equivalent based on available chlorine atoms. Subsequently, the reaction solution was poured into 600 parts of water while being stirred. The obtained solution was heated to 70° C., and was then subjected to filtration, washing with hot water, washing with 1% sodium hydroxide aqueous solution, and washing with hot water in this order. Thereafter, the resultant was dried to obtain 8.8 parts of chlorinated Pigment Yellow 109 having an average number of chlorine atoms, which were further substituted, of 0.25. The yield was 88%. The average number of chlorine substitutions (total) was 8.25. The average particle diameter was 0.04 μm.

Example 15

10 parts of C. I. Pigment Yellow 110 (Irgazin Yellow L2060, manufactured by BASF) which is an isoindolinone pigment and 0.05 parts of iodine were added to and dissolved in 80 parts of 98% sulfuric acid, and thereafter, 1.21 parts of trichloroisocyanuric acid were added to the solution. The obtained mixture was stirred at 10° C. for 3 hours. At this time, the amount of trichloroisocyanuric acid was 0.33 times the mole of Pigment Yellow 110, and was 1.00 molar equivalent based on available chlorine atoms. Subsequently, the reaction solution was poured into 600 parts of water while being stirred. The obtained solution was heated to 70° C., and was then subjected to filtration, washing with hot water, washing with 1% sodium hydroxide aqueous solution, and washing with hot water in this order. Thereafter, the resultant was dried to obtain 8.5 parts of chlorinated Pigment Yellow 109 having an average number of chlorine atoms, which were further substituted, of 0.78. The yield was 91%. The average number of chlorine substitutions (total) was 2.78.

Example 16

10 parts of C. I. Pigment Violet 23 (Lionogen Violet FG-6240, manufactured by TOYOCOLOR CO., LTD.) which is a dioxazine pigment was added to and was dissolved in 100 parts of methanesulfonic acid, and thereafter, 1.32 parts of trichloroisocyanuric acid were added to the solution. The obtained mixture was stirred at 20° C. for 2 hours. At this time, the amount of trichloroisocyanuric acid was 0.33 times the mole of Pigment Violet 23, and was 1.00 molar equivalent based on available chlorine atoms. Subsequently, the reaction solution was poured into 600 parts of water while being stirred. The obtained solution was heated to 70° C., and was then subjected to filtration, washing with hot water, washing with 1% sodium hydroxide aqueous solution, and washing with hot water in this order. Thereafter, the resultant was dried to obtain 10.4 parts of chlorinated Pigment Violet 23 having an average number of chlorine atoms, which were further substituted, of 0.23. The yield was 98%. The average number of chlorine substitutions (total) was 2.23. The average particle diameter was 0.03 μm.

Example 17

10 parts of C. I. Pigment Blue 60 (Lionogen Blue 6510, manufactured by TOYOCOLOR CO., LTD.) which is an indanthrone pigment was added to and was dissolved in 100 parts of methanesulfonic acid, and thereafter, 1.76 parts of trichloroisocyanuric acid were added to the solution. The obtained mixture was stirred at 20° C. for 3 hours. At this time, the amount of trichloroisocyanuric acid was 0.33 times the mole of Pigment Blue 60, and was 1.00 molar equivalent based on available chlorine atoms. Subsequently, the reaction solution was poured into 600 parts of water while being stirred. The obtained solution was heated to 70° C., and was then subjected to filtration, washing with hot water, washing with 1% sodium hydroxide aqueous solution, and washing with hot water in this order. Thereafter, the resultant was dried to obtain 9.8 parts of chlorinated Pigment Blue 60 having an average number of chlorine atoms of 0.71. The yield was 90%. The average particle diameter was 0.05 μm.

Hereafter, coating materials were produced as examples of colored compositions using the halogenated organic pigment of the present invention. The produced coating materials were applied, and their brightness and durability were then evaluated. In order to compare with halogenated organic pigments obtained by conventional methods, three types of pigments, namely, the chlorinated copper phthalocyanine described in Example 5, the crude chlorinated copper phthalocyanine described in Comparative Example 1, and the chlorinated copper phthalocyanine described in Comparative Example 2, all of which had almost the same number of chlorine substitutions, were used for comparative evaluation.

Example 18

6 parts of the halogenated phthalocyanine obtained in Example 5 and 94 parts of a vehicle for coating materials (a mixture of 56 parts of Phthalkid 133-60 (manufactured by Hitachi Chemical Co., Ltd.), 28 parts of Melan 20 (manufactured by Hitachi Chemical Co., Ltd.), and 10 parts of xylene) were dispersed in a 3-mm steel ball to obtain a deep-colored coating material. Separately, 25 parts of Taipek CR-90 (manufactured by ISHIHARA SANGYO KAISHA, LTD.) as an extender pigment and 75 parts of a vehicle for coating materials (a mixture of 47 parts of Phthalkid 133-60 (manufactured by Hitachi Chemical Co., Ltd.), 23 parts of Melan 20 (manufactured by Hitachi Chemical Co., Ltd.), and 5 parts of xylene) were dispersed in a 3 mmφ aluminum ball to obtain a white coating material. Thereafter, 10 parts of the deep-colored coating material were mixed with 24 parts of the white coating material to obtain a light-colored coating material.

The above-described light-colored coating material was applied onto the coating surface of a metal plate (cold rolled steel SPCC-SD, one surface: water-abrasive coating plate, gray electrodeposition painted finish) using a 6-mil applicator, and it was then cured in an oven of 150° C. to produce a coated plate. The color of the coated surface was measured using a colorimeter (Spectro Color Meter SE2000, NIPPON DENSHOKU INDUSTRIES Co., Ltd.). As a result, it was found that brightness was $C^*=49.5$. As described later, this case exhibited a numerical value that was higher than that in the case of using the chlorinated copper phthalocyanine obtained in Comparative Example 2, and higher brightness.

Subsequently, the deep-colored coating material was applied onto the same metal plate as described above using a 6-mil applicator, and it was then hardened in an oven of 150° C. to produce a coated plate. Thereafter, a white coating material was further applied onto the coated plate using a 6-mil applicator, and it was then hardened in an oven of 180° C. to produce a coated plate. The color of the coated surface was measured, and as a result, lightness was $L^*=96.6$. As described later, this case exhibited a numerical value that was higher than that in the case of using the chlorinated copper phthalocyanine obtained in Comparative Example 2.

The chlorinated copper phthalocyanine obtained in Comparative Example 1 or Comparative Example 2 comprises blue aluminum phthalocyanine as an impurity. Thus, it is assumed that this impurity would migrate from the deep-colored coated film to the white coated film (=bleed), and then would color there, and thus that the lightness would be reduced. That is to say, it was revealed that a coating material in which the chlorinated copper phthalocyanine of the present invention is used is excellent in terms of migration resistance that is one type of durability.

Comparative Example 7

For comparison, the same operations as those in Example 18 were carried out, with the exception that the crude chlorinated copper phthalocyanine obtained in Comparative Example 1 was used instead of the chlorinated copper phthalocyanine obtained in Example 5, to produce a deep-colored coating material. However, since the viscosity of the obtained deep-colored coating material was extremely high, it could not be separated from the steel ball, and thus, the deep-colored coating material could not be evaluated as a coating material.

Comparative Example 8

For comparison, the same method as that of Example 18 was carried out, with the exception that the chlorinated copper phthalocyanine obtained in Comparative Example 2 was used instead of the chlorinated copper phthalocyanine obtained in Example 5, to produce a deep-colored coating material and a light-colored coating material. The color of a coated plate produced using the light-colored coating material was measured by the same method as that of Example 18. As a result, brightness was $C^*=45.3$. Further, a white coating material was applied onto a coated plate produced using the deep-colored coating material, and the color of the coated plate was then measured. As a result, lightness was $L^*=92.4$.

Hereafter, plastic colorants were prepared as examples of colored compositions using the halogenated organic pigment of the present invention, and thereafter, colored plastic molded products were produced using the colorants and were then evaluated. In order to compare with halogenated organic pigments obtained by conventional methods, three types of pigments, namely, the chlorinated copper phthalocyanine described in Example 5, the crude chlorinated copper phthalocyanine described in Comparative Example 1, and the chlorinated copper phthalocyanine described in Comparative Example 2, all of which had almost the same number of chlorine substitutions, were used for comparative evaluation.

Example 19

100 parts of the chlorinated copper phthalocyanine obtained in Example 5 were mixed with 100 parts of calcium stearate using a mixing machine to obtain a plastic colorant (dry color). Thereafter, 2 parts of the obtained plastic colorant (thy color) were fully mixed with 1000 parts of high-density polyethylene resin (product name: Hizex2208J, manufactured by Prime Polymer Co., Ltd.) by tumbling with several droplets of adhesive, and the mixture was then molded into a plate-like shape using an injection molding machine. Thereafter, the hue was measured using a colorimeter (Minolta Spectrophotometer CM-2002, manufactured by Konica Minolta, Ink.). The obtained plate was sandwiched between white soft vinyl chloride sheets, and pressurized and heated for 1 minute. After that, the migration property of the colorant into the white soft vinyl chloride was examined. However, migration was not observed. The brightness $C^*$ of the obtained plate was 39.2, and the hue angle h was 256.2°. As described later, the present colorant was more excellent than the case of using the chlorinated copper phthalocyanines obtained in Comparative Example 1 and Comparative Example 2 in migration resistance, and in terms of the hue, redness was more vivid.

Comparative Example 9

For comparison, the same operations as those in Example 19 were carried out, with the exception that the crude chlorinated copper phthalocyanine obtained in Comparative Example 1 was used instead of the chlorinated copper phthalocyanine obtained in Example 5, to obtain a plate-shaped molded product. However, the obtained plate had many green spots, and resulted in a coloring property (vividness) that was extremely poor compared to the case of the plate obtained in Example 19. The spots were observed under a microscope, and confirmed to be pigment particles of undispersed chlorinated copper phthalocyanine.

Comparative Example 10

For comparison, the same operations as those in Example 19 were carried out, with the exception that the chlorinated copper phthalocyanine obtained in Comparative Example 2 was used instead of the chlorinated copper phthalocyanine obtained in Example 5, to obtain a plate-shaped molded product. The color of the obtained plate was measured, and as a result, the brightness $C^*$ was 38.8, the hue angle h was 255.9°, and in comparison to the case of Example 19, the green tinge was less vivid. Moreover, when its migration property was examined, migration was observed. That is to say, migration resistance, which is one type of durability, was poorer in the present comparative example than in the case of Example 19.

Example 20

81 parts of aluminum chloride, 19 parts of sodium chloride, and 1 part of ferric chloride were fused by heating, and 0.1 part of iodine was then added to the mixture, and thereafter, 20 parts of copper phthalocyanine were added to the reaction mixture at 140° C. The temperature of the reaction solution was kept at 130° C., and 5.7 parts of trichloroisocyanuric acid were added to the reaction solution while intensively stirring, and the obtained mixture was then stirred at the same temperature for 4 hours. At this time, the amount of trichloroisocyanuric acid was 0.71 times the mole of copper phthalocyanine, and was 2.1 molar equivalents based on available chlorine atoms. The reaction solution was poured into 1000 parts of water, and the obtained mixture was then subjected to filtration, washing with hot water, washing with 1% hydrochloric acid aqueous solution, washing with hot water, washing with 1% sodium hydroxide aqueous solution, and washing with hot water in this order. Thereafter, the resultant was dried to obtain 21.1 parts of crude chlorinated copper phthalocyanine having an average number of chlorine substitutions of 2.0. The yield was 94%.

Examples 21 to 33

First, an example of producing of a halogenated quinacridone by a simple halogenation reaction of a quinacridone will be described below.

A quinacridone, an N-haloimide compound, and a catalyst were added to the solvent shown in Tables 3 and 4, and a halogenation reaction was then carried out under the reaction conditions shown in Table 5. Subsequently, the reaction solution was poured into 600 parts of water while being stirred, and the obtained solution was then heated to 70° C. The reaction solution was subjected to filtration, washing with hot water, washing with 1% sodium hydroxide aqueous solution, and washing with hot water in this order, and then dried to obtain halogenated quinacridone. In Example 30 and Example 31, the reaction product interacted with sulfate ions because it had a tertiary amino group, and the reaction solution (slurry), to which 600 parts of water had been added, had an extremely poor filtration property. Accordingly, this slurry was converted to a weak alkaline slurry by adding sodium hydroxide, and then subjected to filtration, washing with hot water, and drying to obtain a halogenated quinacridone.

While the number of halogen substitutions was 4 or less, the halogenation reaction progressed almost quantitatively and almost all of the used N-haloimide compounds were consumed, and the yield which was calculated from the yield was 99% which was extremely high. Moreover, various N-haloimide compounds were all granular, white solids, and easily-handled, and almost no gas generation was observed during the halogenation reaction, and a series of operations were extremely easily-handled.

With regard to Table 3, Cinquacia Red Y (manufactured by BASF) was used as an unsubstituted quinacridone, Hostaperm Pink E (manufactured by Clariant) was used as a dimethylquinacridone, and Cinquacia Magenta RT (manufactured by BASF) was used as a dichloroquinacridone.

Dimethoxyquinacridone and dibromoquinacridone used were synthesized according to the production method described in U.S. Pat. No. 2,821,529. As a phthalimidomethylated quinacridone, a synthetic material having a number of substituents of 1.4 obtained by the production method described in Japanese Patent Laid-Open No. 55-108466 was used. As a diethylaminopropylaminosulfonyl quinacridone, a synthetic material having a number of substituents of 1.5 obtained by the production method described in Japanese Patent Laid-Open No. 56-118462 was used. As a diethylaminoethylaminomethylcarbonylaminomethyl quinacridone, a synthetic material having a number of substituents of 1.0 obtained by the production method described in Japanese Patent Laid-Open No. 51-18736 was used.

TABLE 3

| | Solvent | | Quinacridone | |
|---|---|---|---|---|
| Example | Name | Amount charged (parts by mass) | Name | Amount charged (parts by mass) |
| 21 | 98% Sulfuric acid | 150 | Unsubstituted quinacridone | 10 |
| 22 | 98% Sulfuric acid | 150 | Unsubstituted quinacridone | 10 |
| 23 | 98% Sulfuric acid | 150 | Unsubstituted quinacridone | 10 |
| 24 | 98% Sulfuric acid | 150 | Unsubstituted quinacridone | 10 |
| 25 | 98% Sulfuric acid | 150 | Dimethylquinacridone | 10 |
| 26 | 98% Sulfuric acid | 150 | Dimethoxyquinacridone | 10 |
| 27 | Chlorosulfonic acid | 150 | Dichloroquinacridone | 10 |
| 28 | 98% Sulfuric acid | 150 | Dibromoquinacridone | 10 |
| 29 | 98% Sulfuric acid | 150 | Phthalimide quinacridone | 10 |
| 30 | 98% Sulfuric acid | 150 | Diethylaminopropylaminosulfonyl quinacridone | 10 |
| 31 | 98% Sulfuric acid | 150 | Diethylaminoethylaminomethylcarbonylaminomethyl quinacridone | 10 |
| 32 | 98% Sulfuric acid | 150 | Unsubstituted quinacridone | 10 |
| 33 | 98% Sulfuric acid | 150 | Unsubstituted quinacridone | 10 |

TABLE 4

| | N-haloimide compound | | | Catalyst | |
|---|---|---|---|---|---|
| | | Amount charged | | | Amount charged |
| Example | Name | Parts by mass | Molar equivalent | Name | Parts by mass |
| 21 | Trichloroisocyanuric acid | 5.0 | 2.0 | None | None |
| 22 | Sodium dichloroisocyanurate | 2.8 | 0.8 | None | None |
| 23 | Sodium dichloroisocyanurate | 0.7 | 0.2 | None | None |
| 24 | Trichloroisocyanuric acid | 9.9 | 4.0 | None | None |
| 25 | Trichloroisocyanuric acid | 4.6 | 2.0 | None | None |
| 26 | Trichloroisocyanuric acid | 4.2 | 2.0 | None | None |
| 27 | Trichloroisocyanuric acid | 14.0 | 6.9 | Iodine | 0.1 |
| 28 | Trichloroisocyanuric acid | 3.3 | 2.0 | None | None |
| 29 | Trichloroisocyanuric acid | 2.9 | 2.0 | None | None |
| 30 | Trichloroisocyanuric acid | 2.6 | 2.0 | None | None |
| 31 | Trichloroisocyanuric acid | 3.1 | 2.0 | None | None |
| 32 | Tribromoisocyanuric acid | 7.8 | 2.0 | None | None |
| 33 | Potassium dibromoisocyanurate | 5.2 | 1.0 | None | None |

TABLE 5

| Example | Reaction temperature (° C.) | Reaction time (hr) | Yield (parts by mass) | Number of chlorine substitutions (average) | Number of bromine substitutions (average) | Yield (% by mass) |
|---|---|---|---|---|---|---|
| 21 | 20 | 3 | 12.1 | 2.0 | — | 99 |
| 22 | 20 | 3 | 10.8 | 0.8 | — | 99 |
| 23 | 20 | 2 | 10.1 | 0.2 | — | 99 |
| 24 | 20 | 3 | 14.2 | 4.0 | — | 99 |
| 25 | 20 | 3 | 11.9 | 2.0 | — | 99 |
| 26 | 20 | 3 | 11.7 | 2.0 | — | 99 |
| 27 | 30 | 5 | 12.3 | 8.0 | — | 71 |
| 28 | 20 | 3 | 11.3 | 2.0 | 2.0 | 99 |
| 29 | 20 | 3 | 11.1 | 2.0 | — | 98 |
| 30 | 20 | 3 | 10.8 | 2.0 | — | 97 |
| 31 | 20 | 3 | 11.0 | 2.0 | — | 97 |
| 32 | 20 | 3 | 14.9 | — | 2.0 | 99 |
| 33 | 20 | 3 | 12.4 | — | 1.0 | 99 |

Example 34

An example of producing a chlorinated quinacridone by a chlorination reaction of a quinacridone comprising a substitution of —SO$_3$H groups will be described below. In this example, an example of producing dichloroquinacridone sulfonic acid in which a sulfonation reaction and a chlorination reaction are continuously carried out will be described.

10 parts of unsubstituted quinacridone were added to a mixed solution of 100 parts of 98% sulfuric acid and 50 parts of 30% fuming sulfuric acid, and the obtained mixture was then stirred at 60° C. for 2 hours to carry out a sulfonation reaction. Subsequently, the temperature was decreased to 25° C., 5 parts of trichloroisocyanuric acid were then added to the reaction mixture, and the obtained mixture was then stirred at the same temperature for 3 hours. The amount of trichloroisocyanuric acid was 0.67 times the mole of the used quinacridone, and was 2.0 molar equivalents based on available chlorine atoms. The reaction solution was poured into 600 parts of water while being stirred, and the obtained mixture was then subjected to filtration and washing with water to obtain water paste, which was added to 500 parts of water to prepare slurry. A 25% sodium hydroxide aqueous solution was added to the slurry to adjust the pH to 11, and the mixture was then subjected to filtration, washing with water, and drying to obtain 16.1 parts of chlorinated quinacridone (yield: 98%).

This chlorinated quinacridone had a number of chlorine substitutions of 2.0 and a number of —SO$_3$Na groups substituted of 1.3, and was a compound having the same composition as that of the dichloroquinacridone sulfonic acid disclosed in Japanese Patent Laid-Open No. 2005-206630.

Example 35

An example of producing a chlorinated quinacridone using a chlorination reaction of a quinacridone comprising a substitution of —$SO_2Cl$ groups will be described below. In this example, a production example in which a chlorosulfonation reaction and a chlorination reaction are continuously carried out to produce dichloroquinacridone sulfonyl chloride, and an amination reaction is then carried out will be described.

10 parts of unsubstituted quinacridone were added to 150 parts of chlorosulfonic acid, and a chlorosulfonation reaction was carried out by stirring the obtained mixture at 40° C. for 2 hours. Subsequently, the temperature was decreased to 25° C., 5 parts of trichloroisocyanuric acid were then added to the reaction mixture, and the obtained mixture was then stirred at the same temperature for 3 hours. The amount of trichloroisocyanuric acid was 0.67 times the mole of the used quinacridone, and was 2.0 molar equivalents based on available chlorine atoms. 6 parts of thionyl chloride were further added to the reaction mixture, and the obtained mixture was then stirred at the same temperature for 1 hour. The reaction solution was poured into 1000 parts of ice water, and then subjected to filtration and washing with water to obtain water paste, which was then added to 500 parts of water to prepare slurry. 13 parts of diethylaminopropylamine were added to the slurry, and the mixture was then stirred at 60° C. for 5 hours, and was then subjected to filtration, washing with water, and drying to obtain 20.6 parts of chlorinated quinacridone (yield: 98%). This chlorinated quinacridone had a number of chlorine substitutions of 2.0 and a number of diethylaminopropylaminosulfonyl groups (—$SO_2NH(CH_2)_3N(C_2H_5)_2$) of 1.5, and was a compound having the same composition as that of the compound of Example 30.

Example 36

An example of producing a chlorinated quinacridone using a chlorination reaction of a quinacridone comprising a substitution of —$CH_2NHCOCH_2Cl$ will be described below. In this example, a production example in which a chloroacetamidemethylation reaction and a chlorination reaction are continuously carried out to produce a dichloro(chloroacetamidemethyl) quinacridone, and an amination reaction is then carried out will be described.

10 parts of unsubstituted quinacridone, 4.5 parts of chloroacetamide, and 1.5 parts of paraformaldehyde were added to 150 parts of 98% sulfuric acid, and the obtained mixture was then stirred at 20° C. for 4 hours to carry out a chloroacetamidemethylation reaction. Subsequently, 5 parts of trichloroisocyanuric acid were added to the reaction mixture, and the obtained mixture was then stirred at the same temperature for 3 hours. The amount of trichloroisocyanuric acid was 0.67 times the mole of the used quinacridone, and was 2.0 molar equivalents based on available chlorine atoms. The reaction solution was poured into 1000 parts of ice water, and then subjected to filtration and washing with water to obtain water paste, which was then added to 500 parts of water to prepare slurry. 8 parts of diethylaminoethylamine were added to the slurry, and thereafter, the mixture was stirred at 60° C. for 5 hours, and was then subjected to filtration, washing with water, and drying to obtain 17.8 parts of chlorinated quinacridone (yield: 98%). This chlorinated quinacridone had a number of chlorine substitutions of 2.0 and a number of diethylaminoethylaminomethylcarbonylaminomethyl groups (—$CH_2NHCOCH_2NHC_2H_4N(C_2H_5)_2$) substituted of 1.0, and was a compound having the same composition as that of the compound of Example 31.

Example 37

A production example in which the production method of the present invention is incorporated into the production process of a quinacridone will be described below. In this example, an example of producing a dichloroquinacridone in which a ring-closure reaction and a chlorination reaction are continuously carried out will be described.

In accordance with an ordinary method, 10 parts of 2,5-dianilinoterephthalic acid were added to 150 parts of polyphosphoric acid, and the obtained mixture was then stirred at 125° C. for 3 hours for ring-closing to obtain a polyphosphoric acid solution of unsubstituted quinacridone. Subsequently, the temperature was decreased to 50° C., and 4.5 parts of trichloroisocyanuric acid were then added to the solution, and the obtained mixture was stirred at the same temperature for 2 hours. The amount of trichloroisocyanuric acid was 0.67 times the mole of the used quinacridone, and was 2.0 molar equivalents based on available chlorine atoms. The reaction solution was poured into 600 parts of water at 50° C., and was then subjected to filtration, washing with hot water, washing with 1% sodium hydroxide aqueous solution, and washing with hot water in this order, and thereafter, was dried to obtain 11.5 parts of chlorinated quinacridone (yield: 96%). This chlorinated quinacridone had a number of chlorine substitutions of 2.0, and was a compound having the same composition as that of the compound of Example 21.

Example 38

Next, a production example in which the chlorinated quinacridone obtained according to the production method of the present invention was treated with a solvent to process it into a pigment will be described below.

100 parts of the chlorinated quinacridone obtained in Example 21 above were added to 2000 parts of N,N-dimethylformamide, and the obtained mixture was stirred at 120° C. to 140° C. for 3 hours, and then subjected to filtration, washing with water, and drying to obtain a chlorinated quinacridone that was processed into a pigment.

The chlorinated quinacridone that was processed into a pigment was observed under an electron microscope, and the average particle diameter of the pigment particles was found to be 0.025 µm. The chlorinated quinacridone obtained by the conventional production method, which will be described later in Comparative Example 11, was also observed under an electron microscope, and the average particle diameter of the pigment particles was found to be 0.034 µm, and thus, the chlorinated quinacridone according to the present invention was finer than that of Comparative Example 11. In addition, the chlorinated quinacridones of Comparative Example 11 were all dichloroquinacridones, whereas the chlorinated quinacridones according to the present invention were mixtures of monochloroquinacridones, dichloroquinacridones and trichloroquinacridones at a ratio of 1:2:1 (molar ratio). Accordingly, it is considered that the crystallinity was reduced and small particle diameters were thereby obtained.

Next, in order to evaluate the performance as a coloring material, an offset ink was produced, and the color tone was then evaluated. 2 parts of offset ink varnish consisting of 0.5 parts of the chlorinated quinacridone that had been processed into a pigment, 0.45 parts of rosin modified phenolic resin (TAMANOL, manufactured by Arakawa Industrial Japan), and 1.05 parts of AF Solvent 7 (manufactured by JX Nippon Oil & Energy Corporation) as a solvent was kneaded using a hoover muller (manufactured by Toyo Seiki Co., Ltd.) with 150 pounds (68 kg) loaded to produce a red ink. Separately, 2 parts of titanium dioxide (R-680, manufactured by ISHIHARA SANGYO KAISHA, LTD.) and 3 parts of offset ink varnish (a mixture consisting of 0.9 parts of the above-described rosin modified phenolic resin and 2.1 parts of the AF Solvent 7) were also kneaded in the same manner to produce a white ink. Subsequently, the above-described red ink and the white ink were mixed with each other to produce a light red ink, and the obtained ink was then sandwiched between two transparent films to prepare a colorimetric sample.

Regarding colorimetry, L* value (lightness), h value (hue angle), and C* value (brightness) were measured using a colorimeter (Spectro Color Meter SE2000, manufactured by Nippon Denshoku Industries Co., Ltd.). The L* value is increased as the mixing ratio of the white ink to the red ink is gradually increased; however, the h value is also increased, meaning that the color becomes a yellowish color, and the C* value is also decreased. For these reasons, absolute evaluation is difficult. Thus, the mixing ratio of the white ink was adjusted so that the L* value could be kept at constant, and the color was measured, color tone was evaluated by using the h value and C* value at this point. The reciprocal of the mixing ratio of the white ink was adopted as a coloring strength.

Table 6 shows the evaluation results, the numerical values of which were obtained when the L* value was 55. The chlorinated quinacridone according to the present invention was not so different from the after-mentioned Comparative Example 11 in terms of hue; however, it had higher brightness and was excellent in terms of coloring strength.

TABLE 6

| | h value (hue angle) | C* value (brightness) | Coloring strength |
|---|---|---|---|
| Example 38 | 342.2° | 53.1 | 112% |
| Comparative Example 11 | 342.4° | 50.9 | Comparison standard |

Comparative Example 11

A production example in which the chlorinated quinacridone obtained by the conventional production method using chloroaniline as a raw material is treated with a solvent to process it into a pigment will be described below.

100 parts of dichloroquinacridone (Cinquacia Magenta RT, manufactured by BASF) were added to and dissolved in 1500 parts of 98% sulfuric acid, and the obtained mixture was then stirred at 20° C. for 3 hours, and thereafter, was poured into 6000 parts of water while stirring. The obtain solution was then heated to 70° C., and then subjected to filtration, washing with hot water, washing with 1% sodium hydroxide aqueous solution, and washing with hot water in this order, and then dried. Subsequently, the resultant was added to 2000 parts of N,N-dimethylformamide, and the obtained mixture was then stirred at 120° C. to 140° C. for 3 hours, and subjected to filtration, washing with water, and drying to obtain a chlorinated quinacridone that was processed into a pigment.

Example 39

The same operations as those in Example 38 were carried out with the exception that the chlorinated quinacridone obtained in Example 22 was used instead of the chlorinated quinacridone obtained in Example 21 to obtain a chlorinated quinacridone that was processed into a pigment.

The chlorinated quinacridone that was processed into a pigment was subjected to X-ray diffraction measurement using an X-ray diffraction measurement device (MiniFlexII, manufactured by Rigaku Corporation). Regarding the main peaks, Bragg angles of CuKα X-ray diffraction were at 6.2°, 13.2°, 24.0°, and 26.4°, and these were peaks almost identical to those of the solid solution shown in Table 3 of U.S. Pat. No. 3,160,510. When the chlorinated quinacridone of Example 22 was subjected to X-ray diffraction measurement before it was processed into a pigment, Bragg angles of its main peaks were completely identical to those as described above. This chlorinated quinacridone had a number of chlorine substitutions of 0.8, and as a result of analysis, this chlorinated quinacridone comprised approximately 35% of unsubstituted quinacridone; however, since neither α-type, nor γ-type unsubstituted quinacridone was detected by the X-ray diffraction measurement, it was confirmed that a solid solution was formed. Moreover, since no change was found in the peaks of X-ray diffraction before and after a solvent treatment, it was confirmed that the solid solution had stable crystals.

Example 40

The same operations as those in Example 38 were carried out with the exception that the chlorinated quinacridone obtained in Example 23 was used instead of the chlorinated quinacridone obtained in Example 21 to obtain a chlorinated quinacridone that was processed into a pigment.

When this chlorinated quinacridone that was processed into a pigment was observed under an electron microscope, the average particle diameter of the particles was 0.14 μm. In the after-mentioned Comparative Example 12, unchlorinated, unsubstituted quinacridone was treated with sulfuric acid in accordance with Example 23, and the resultant was then subjected to the same operations as those of Example 38 to process it into a pigment. The average particle diameter of the particles, which was measured by observation under an electron microscope, was 0.36 μm. That is to say, the chlorinated quinacridone that had been processed into a pigment according to the present invention had a number of chlorine substitutions of 0.2, and as a result of the analysis, a majority thereof was unsubstituted quinacridone in which chlorine atoms were not substituted; however, it was confirmed that the particles were effectively miniaturized because of the presence of chlorinated quinacridone contained in a small amount.

X-ray diffraction measurement was performed as in the case of Example 39, and it was found that both of Example 40 and Comparative Example 12 were γ-type crystals.

Next, the results obtained by producing an offset ink and evaluating the color tone thereof, as in Example 38, are shown in Table 7.

The chlorinated quinacridone according to the present invention was not so different from the after-mentioned Comparative Example 12 in terms of hue; however, it had high brightness and was excellent in terms of coloring strength. That is, by slightly chlorinating a quinacridone according to the production method of the present invention, the present chlorinated quinacridone could be prepared to have excellent color tone while maintaining the essential physical properties of the quinacridone before chlorination.

TABLE 7

|  | h value (hue angle) | C* value (brightness) | Coloring strength |
|---|---|---|---|
| Example 40 | 352.9° | 50.2 | 125% |
| Comparative Example 12 | 353.3° | 47.8 | Comparison standard |

Comparative Example 12

A production example in which an unsubstituted quinacridone is treated with a solvent after completion of a sulfuric acid treatment to process it into a pigment will be described below.

10 parts of an unsubstituted quinacridone (Cinquacia Red Y, manufactured by BASF) were added to and dissolved in 150 parts of 98% sulfuric acid, and the obtained mixture was then stirred at 20° C. for 3 hours. Thereafter, the reaction solution was poured into 600 parts of water while stirring, and then heated to 70° C., and thereafter, subjected to filtration, washing with hot water, washing with 1% sodium hydroxide aqueous solution, and washing with hot water in this order, and then dried. Subsequently, the resultant was added to 200 parts of N,N-dimethylformamide, and then stirred at 120° C. to 140° C. for 3 hours, and was then subjected to filtration, washing with water, and drying to obtain an unsubstituted quinacridone that was processed into a pigment.

Example 41

An example of using a color toner will be described below as an example of a colored composition comprising the chlorinated quinacridone of the present invention and a vehicle component.

50 parts of the chlorinated quinacridone obtained in Example 38 and 50 parts of polyester resin (polyester resin A described in Example 1 of Japanese Patent Laid-Open No. 2012-198438) were mixed with each other at 120° C. using a pressure kneader, and thereafter, the mixture was kneaded at 95° C. using a triple roll mill to obtain a colored composition. 10 parts of this colored composition, 87.5 parts of polyester resin (polyester resin A described in Example 1 of Japanese Patent Laid-Open No. 2012-198438), 1 part of charge control agent (3,5-di-tert-butyl salicylic acid calcium salt), and 1.5 parts of releasing agent (ethylene homopolymer; weight average molecular weight: 850; degree of dispersion: 1.08; melting point: 107° C.) were mixed using a Henschel mixer, and the thus obtained mixture was then melted and kneaded at 120° C. using a twin screw extruder. Thereafter, the reaction mixture was crushed using a crusher, and was then classified to obtain fine base toner particles having an average particle diameter of 5 to 10 μm. 0.5 parts of hydrophobic titanium oxide (STT-30A, manufactured by Titan Kogyo, Ltd.) were further added to and mixed with the base toner particles to obtain a color toner A.

Separately, the same operations as those described above were carried out with the exception that the chlorinated quinacridone obtained in Comparative Example 11 was used instead of the chlorinated quinacridone obtained in Example 38 to obtain a color toner B.

These color toners were each fused by hot pressing, and a uniform thin layer was then produced on a glass board. Transparency was evaluated by visual observation, and it was found that the transparency of the color toner A was higher than that of the color toner B.

Thereafter, 6 parts of each color toner were mixed with 100 parts of ferrite carrier (DFC-350C, manufactured by DOWA IP CREATION Co., Ltd.) coated with a silicone resin having an average particle diameter of 60 μm, used as a carrier, to produce a developer. Thereafter, using the developer, an image was printed on a copy paper (Color Application Paper Ncolor 127, A4 size, 127 g/m$^2$, manufactured by Fuji Xerox Co., Ltd.) employing a copying machine (CLC-730, manufactured by Canon) to produce a printed article. These printed articles were evaluated by visual observation, and it was found that the printed article produced using the color toner A was more excellent in terms of brightness, and was highly dense as compared with the printed article produced using the color toner B.

Example 42

An example of using an inkjet ink will be described below as an example of a colored composition comprising the chlorinated quinacridone of the present invention and a vehicle component.

19 parts of the chlorinated quinacridone obtained in Example 38, 16.4 parts of styrene-acrylic acid copolymer (JONCRYL 61J; weight average molecular weight: 10000; acid value: 195 mgKOH/g; solid content: 31%; manufactured by BASF), 5 parts of nonionic surfactant (polyoxyethylenedistyrene phenyl ether; Emulgen A-90; manufactured by Kao Corporation), and 59.6 parts of ion exchange water were mixed with one another, and zirconia beads (diameter: 0.5 mmφ) were then added thereto, and the obtained mixture was dispersed using a paint shaker for 12 hours to produce a condensate. Thereafter, 12.5 parts of this condensate, 2.5 parts of styrene-acrylic acid copolymer (Emapoly TYN-40; solid content: 44.8%; manufactured by Gifu Shellac Manufacturing Co., Ltd.), 2.0 parts of nonionic surfactant (polyoxyethylenedistyrene phenyl ether; Emulgen A-90; manufactured by Kao Corporation), and 64.9 parts of ion exchange water were mixed with one another, and diethylene glycol monobutyl ether was then added to the mixture, as appropriate, to adjust the viscosity to 2.5 cps (the value measured at 25° C. by an E-type viscometer) and the surface tension to 40 dyne/cm. After that, the mixture was filtrated through a 1.0-μm membrane filter, and was further filtrated through a 0.45-μm membrane filter to produce an inkjet ink A.

Separately, the same operations as those described above were carried out with the exception that the chlorinated quinacridone obtained in Comparative Example 11 was used instead of the chlorinated quinacridone obtained in Example 38 to obtain an inkjet ink B. These inkjet inks were each filled into an ink cartridge (HG5130, manufactured by SEIKO EPSON CORPORATION), and a color chart image (chart image "TC3.5 CMYK i1_iO" for ProfileMaker, manufactured by X-rite) was printed at a resolution of 600×600 dpi on a high-quality paper (npi high-quality; basis weight: 64.0 g/m$^2$; manufactured by NIPPON PAPER INDUSTRIES CO., LTD.) and on a coated paper (OK Top Coat; basis weight: 104.7 g/m$^2$; manufactured by Oji Paper Co., Ltd.) to obtain printed articles. The printed articles were evaluated by visual observation, and it was found that the inkjet ink A was more excellent in terms of brightness, and was also highly dense as compared with the inkjet ink B.

Example 43

An example of using a color filter resist ink will be described below as an example of a colored composition comprising the chlorinated quinacridone of the present invention and a vehicle component.

10.5 parts of the chlorinated quinacridone obtained in Example 38, 1.5 parts of the chlorinated quinacridone produced in Example 35 as a dispersion aid, 23 parts of acrylic resin solution (acrylic resin solution 1 described in the Examples of Japanese Patent Laid-Open No. 2013-120309), 3.6 parts of AJISPER PB821 (manufactured by Ajinomoto Fine-Techno Co., Inc.) as a dispersant, and 61.4 parts of propylene glycol monomethyl ether acetate were mixed with one another, and zirconia beads (diameter: 0.1 mmφ) were then added thereto, and the obtained mixture was then dispersed using PICO MILL (manufactured by ASADA IRON WORKS, CO., LTD.) for 8 hours to produce a condensate.

40 parts of this condensate, 213.2 parts of acrylic resin solution (acrylic resin solution 2 described in the Examples of Japanese Patent Laid-Open No. 2013-120309), 2.8 parts of photopolymerizable monomer (ARONIX M400, manufactured by TOAGOSEI CO., LTD.), 2 parts of photopolymerization initiator (IRGACURE 907, manufactured by BASF), 0.4 parts of sensitizer (EAB-F, manufactured by HODOGAYA CHEMICAL CO., LTD.), and 39.6 parts of ethylene glycol monomethyl ether acetate were mixed with one another, and the thus obtained mixture was then filtrated through a 1-μm filter to produce a color filter resist ink A.

Separately, the same operations as those described above were carried out with the exception that the chlorinated quinacridone obtained in Comparative Example 11 was used instead of the chlorinated quinacridone obtained in Example 38 to obtain color filter resist ink B.

These color filter resist inks were each applied onto a glass board having a thickness of 0.7 mm so as to result in a film thickness of 1.5 μm to produce a coated board, and thereafter, it was dried, and then irradiated with ultraviolet rays (300 mJ/cm$^2$). Thereafter, it was heated at 230° C. for 1 hour to obtain a color filter.

The evaluation of the obtained color filter was determined based on the numerical value of the contrast ratio. The contrast ratio was calculated by sandwiching the color filter between two polarizing plates, then measuring the luminance of the color filter using a chromameter (BM-5A, manufactured by TOPCON CORPORATION), and then dividing the luminance when the polarizing plates were disposed in parallel by the brightness when the polarizing plates are disposed orthogonally.

As a result, the contrast ratio of the color filter produced using the color filter resist ink A was 3500, and the contrast ratio of the color filter produced using the color filter resist ink B was 1700, and the color filter resist ink A was superior to the color filter resist ink B.

INDUSTRIAL APPLICABILITY

The method for producing a halogenated organic pigment of the present invention does not need special production equipment, equipment for treating by-products or the like, and it is excellent in terms of safety and productivity. A halogenated organic pigment obtained by the production method of the present invention has a color tone of which the adjustable range is wide. Thus, according to the present invention, a colored composition which can be used for a wide range of applications and is excellent in terms of usefulness can be provided.

The invention claimed is:

1. A method for producing a halogenated organic pigment, the method comprising halogenating an organic pigment with a halogenating agent in the presence of a solvent comprising a strong acid,
wherein:
the halogenating agent comprises at least one N-haloimide compound selected from the group consisting of trichloroisocyanuric acid, a metal salt of dichloroisocyanuric acid, tribromoisocyanuric acid, and a metal salt of dibromoisocyanuric acid; and
the strong acid comprises at least one selected from the group consisting of sulfuric acid, fuming sulfuric acid, chlorosulfonic acid, polyphosphoric acid, and methanesulfonic acid.

2. The method according to claim 1, wherein the N-haloimide compound comprises at least one selected from the group consisting of trichloroisocyanuric acid and sodium dichloroisocyanurate.

3. The method according to claim 1, wherein the solvent further comprises an eutectic salt.

4. The method according to claim 3, wherein the eutectic salt comprises aluminum chloride and sodium chloride.

5. The method according to claim 1, wherein the organic pigment comprises at least one selected from the group consisting of a quinacridone pigment, a phthalocyanine pigment, an anthraquinone pigment, a quinophthalone pigment, a perylene pigment, an isoindolinone pigment, a dioxazine pigment and an indanthrone pigment.

6. The method according to claim 5, wherein the organic pigment comprises a quinacridone compound represented by the following Formula (I):

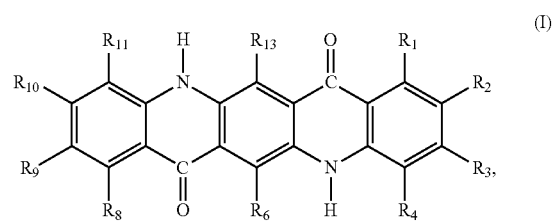

wherein:
$R_1$ to $R_4$, $R_6$, $R_8$ to $R_{11}$, and $R_{13}$ each independently represent any one selected from the group consisting of a hydrogen atom, a chlorine atom, a bromine atom, a C1-C4 alkyl group, a C1-C4 alkoxy group, a phthalimidomethyl group, —CH$_2$NHCOCH$_2$Cl, —SO$_2$Cl, —SO$_3$M, and —X1-X2-N(X3)$_2$;
M represents a hydrogen atom or an alkali metal;
X1 represents —SO$_2$NH— or —CH$_2$NHCOCH$_2$NH—;
X2 represents a C1-C4 alkylene group;
X3 represents a C1-C4 alkyl group optionally having a heteroatom, wherein X3 groups may be connected to each other to form a ring; and
at least one of $R_1$ to $R_4$, $R_6$, $R_8$ to $R_{11}$, and $R_{13}$ is a hydrogen atom.

* * * * *